(12) United States Patent
Horiuchi et al.

(10) Patent No.: US 8,663,560 B2
(45) Date of Patent: Mar. 4, 2014

(54) FLOW CELL AND LIQUID DELIVERY METHOD

(75) Inventors: Tsutomu Horiuchi, Atsugi (JP); Toru Miura, Atsugi (JP); Yuzuru Iwasaki, Atsugi (JP); Michiko Seyama, Atsugi (JP); Tsuyoshi Hayashi, Atsugi (JP); Jun-ichi Takahashi, Atsugi (JP); Tsuneyuki Haga, Atsugi (JP)

(73) Assignee: Nippon Telegraph and Telephone Corporation, Tokyo (JP)

(*) Notice: Subject to any disclaimer, the term of this patent is extended or adjusted under 35 U.S.C. 154(b) by 386 days.

(21) Appl. No.: 12/993,298

(22) PCT Filed: May 26, 2009

(86) PCT No.: PCT/JP2009/059577
§ 371 (c)(1),
(2), (4) Date: Nov. 18, 2010

(87) PCT Pub. No.: WO2009/145172
PCT Pub. Date: Dec. 3, 2009

(65) Prior Publication Data
US 2011/0070655 A1    Mar. 24, 2011

(30) Foreign Application Priority Data

May 29, 2008 (JP) ................. 2008-141463
May 29, 2008 (JP) ................. 2008-141464

(51) Int. Cl.
*G01N 33/00* (2006.01)
(52) U.S. Cl.
USPC ............... 422/68.1; 422/82.01; 422/82.05; 422/502; 422/503

(58) Field of Classification Search
USPC ................. 422/50, 68.1, 82.01, 82.02, 82.03, 422/82.04, 82.05, 82.06, 82.07, 82.08, 422/82.09, 500, 502, 503; 436/164, 165, 436/180; 435/287.1, 288.7
See application file for complete search history.

(56) References Cited

U.S. PATENT DOCUMENTS

| 2004/0096358 A1 | 5/2004 | Blankenstein et al. |
| 2004/0184964 A1 | 9/2004 | Watanabe et al. |

(Continued)

FOREIGN PATENT DOCUMENTS

| EP | 1 500 937 A1 | 1/2005 |
| EP | 1 795 898 A1 | 6/2007 |

(Continued)

OTHER PUBLICATIONS

Martin Zimmermann, Heinz Schmid, Patrick Hunziker and Emmanuel Delamarche, "Capillary pumps for autonomous capillary systems", The Royal Society of Chemistry 2007, Lab Chip, 2007, vol. 7, pp. 119-125, First published as an Advance Article on the web Oct. 17, 2006.

(Continued)

*Primary Examiner* — Christopher A Hixson
(74) *Attorney, Agent, or Firm* — Harness, Dickey & Pierce, P.L.C.

(57) ABSTRACT

A flow cell includes: a flow channel through which a sample solution flows; an inlet section which communicates with the flow channel and to which the sample solution is supplied; a transfer section which includes a plurality of opening sections, one end side of which communicates with the flow channel and an other side of which opens to outside air, and which communicates with the flow channel, and draws in and guides the sample solution supplied into the inlet section to the flow channel; a detecting section which faces the sample solution in the flow channel; and a sealing member which unsealably seals at least either one of the opening section or the inlet section.

11 Claims, 19 Drawing Sheets

(56) References Cited

U.S. PATENT DOCUMENTS

2005/0282290 A1* 12/2005 Fujimoto et al. ............ 436/180
2006/0043284 A1 3/2006 Baba et al.
2006/0292039 A1 12/2006 Iida

FOREIGN PATENT DOCUMENTS

| JP | 07-063678 A | 3/1995 |
| JP | 11-160229 A | 6/1999 |
| JP | 2002-148187 A | 5/2002 |
| JP | 2004-170408 | 6/2004 |
| JP | 2004-286501 | 10/2004 |
| JP | 2006-078364 | 3/2006 |
| JP | 2006-337221 | 12/2006 |
| WO | 03/093836 | 11/2003 |
| WO | 2004/051228 | 6/2004 |
| WO | 2005/024437 | 3/2005 |
| WO | 2007/149042 A1 | 12/2007 |

OTHER PUBLICATIONS

Decision of Rejection, Japanese Patent Application No. 2010-514482, Jun. 4, 2013.

* cited by examiner

FLOW CELL AND LIQUID DELIVERY METHOD

TECHNICAL FIELD

The present invention relates to a flow cell and a liquid delivery method. Priority is claimed on Japanese Patent Application No. 2008-141463, filed May 29, 2008, and Japanese Patent Application No. 2008-141464, filed May 29, 2008, the contents of which are incorporated herein by reference.

BACKGROUND ART

Measurement which uses a function for identifying highly advanced biologic molecules such as an antigen-antibody reaction and a bond between a DNA fragment (DNA probe) and a DNA, is an important technique in measurement in the areas of clinical testing and biochemistry and in environmental pollutant measurement. Examples of this type of measurement include micro TAS (Total Analysis Systems), micro combinatorial chemistry, chemical IC, chemical sensors, biosensors, microanalysis, electrochemical analysis, QCM measurement, SPR measurement, and ATR measurement. In the area of these types of measurement, the amount of a measurement target sample solution is very small in many cases.

In the type of measurement mentioned above, there is used a sample cell capable of holding a sample solution therein (for example, refer to Patent document 1). Further, a trace amount of a sample solution is supplied to the sample cell, and is flowed and transferred to a detecting section which performs measurement of this sample cell. As a result, measurement is performed at a high level of sensitivity and efficiency without reducing the concentration of a test specimen (DNA, antibody, or the like), which is dissolved or dispersed in a sample solution. This sample cell which flows a sample solution to a measurement portion in this manner is called a flow cell.

Examples of techniques for realizing transport of a trace amount of a sample solution with a flow cell include the methods described below. That is to say, there are methods including: a method in which there is provided a flow channel facing a flow cell detecting section, and a sample solution is transferred with external pressure from a syringe pump or the like; a transferring method with electrostatic force; an electrowetting method; a method of transferring a solution using volume change or air-bubble generation caused by heat application; and a method of utilizing electroosmotic flow.

Moreover, in recent years, there has been proposed a technique for forming a region in a flow cell which serves a flow channel or a pump capable of exerting capillary action on a sample solution (refer to Non-patent document 1). A flow cell fabricated using this technique is such that along the planar direction of the plate-shaped cell, there are formed and linearly arranged an introducing opening (inlet section) to which a sample solution is introduced, a capillary pump (transfer section) which draws in the introduced sample solution, and a flow channel for measurement which is provided between these introducing opening and capillary pump.

If a sample solution is supplied to this flow cell, the sample solution flows from the introducing opening to the capillary pump through the flow channel, and is drawn in by the capillary pump so as to continuously flow through the flow channel.

Moreover, in general, in a case of detecting a test specimen of a sample solution, a measurement result of a measurement target sample solution is compared with a measurement result of a reference solution having properties approximate to those of the sample solution, and the test specimen in the sample solution is measured by the difference therebetween. In a case of performing this type of measurement with a flow cell, it is not easy to provide a system of the sample solution and a system of the reference solution on the same cell. Therefore, in general, first, a reference solution is flowed to the flow channel of the flow cell and a first measurement is performed on this reference solution to thereby find a result. Subsequently, the sample solution is flowed and a measurement is performed to thereby find a result. Next, after having performed a second measurement of the reference solution and analyzed a result thereof, a measurement result of the sample solution is analyzed, using the first and second measurement results of the reference solution.

Incidentally, in the type of measurement mentioned above, having supplied the reference solution to the inlet section, the operator needs to continuously supply the sample solution upon determining the moment at which the reference solution has been drawn into the transfer section and transfer thereof from the inlet section has been completed. Similarly, upon determining the moment at which transfer of the supplied sample solution has been completed, a second supply of the reference solution needs to be made continuously. That is to say, when sequentially supplying different solutions to the inlet section, the operation needs to be performed with attention to the timing and amount of liquid delivery, so that the solutions do not get mixed with each other as much as possible and no air gap is formed between the different solutions flowing through the flow channel.

Here, in a state where the solution is sufficiently accumulated in the inlet section, if the next different solution is supplied, these solutions are mixed with each other, making it difficult to ensure a sufficient level of measurement precision. Moreover, if the next solution is supplied to the inlet section in a state where all of the solution in the inlet section has been transferred and the inlet section is empty, an air gap is formed between these solutions, so that a significant variation in the measurement result referred to as a so-called injection shock occurs. Accordingly, it becomes difficult to make a comparison in the trace amount of variation between the measurement result of the reference solution and the measurement result of the sample solution, so that the level of measurement precision cannot be ensured. Consequently, a high level of proficiency is required for an operator in this type of operation.

Moreover, in general, in this type of measurement which uses a flow cell, a plurality of measurement devices are used and measurements are performed in parallel. Therefore, in a case where a single operator is operating the plurality of measurement devices, the burden on the operator is significant.

Furthermore, since the operation is complex, a series of measurements, in which a plurality of sample solutions are continuously measured, cannot be performed quickly and measurement intervals become long, so that workability is obstructed.

Moreover, in general, in a case of detecting a test specimen of a sample solution, a measurement result of a measurement target sample solution is compared with a measurement result of a reference solution having properties approximate to those of the sample solution, and the test specimen in the sample solution is measured by the difference therebetween. In a case of performing this type of measurement with a flow cell, it is necessary to provide a system of the sample solution and a system of the reference solution on the same cell. However, in this case, the structure of the flow cell becomes complex.

Therefore, in general, first, a reference solution is flowed to the flow channel of the flow cell and a measurement is performed on this reference solution to thereby find a result, and, subsequently, after having flowed a sample solution and performed a measurement to thereby find a result, the measurement result of the reference solution and the measurement result of the sample solution are compared.

As mentioned above, in order to respectively supply a reference solution and sample solution to a flow cell, for example, a plurality of syringe pumps are used. Specifically, these syringe pumps are respectively connected via tubes or the like to the liquid inlet side of a liquid switch, the liquid outlet side of the liquid switch is connected to the flow cell, and the liquid switch is switched for each solution, to thereby perform supply to the flow cell.

However, when respectively supplying the reference solution and the sample solution to the flow cell, if syringe pumps, the liquid switch, the tube, and the like are used as described above, there is a problem in that the configuration of the device becomes complex and consequently the cost of equipment increases. Moreover, in order to ensure the level of measurement precision, there are laborious tasks which need to be performed for each sample solution measurement, such as replacing, cleaning, and drying these syringe pumps, the liquid switch, the tube and the like, and this obstructs measurement workability.

Furthermore, in those cases where an operator uses a pipette to respectively supply a reference solution and a sample solution to a flow cell, having supplied the reference solution to the inlet section, the operator needs to continuously supply the sample solution upon determining the moment at which the reference solution has been drawn into the transfer section and transfer thereof from the inlet section has been completed. That is to say, when sequentially supplying different solutions to the inlet section, the operation needs to be performed so that the solutions do not get mixed with each other as much as possible and no air gap is formed between the different solutions flowing through the flow channel.

Here, if the sample solution is supplied in a state where the reference solution is sufficiently accumulated in the inlet section, these solutions are mixed with each other, making it difficult to ensure the level of measurement precision. Moreover, if the sample solution is supplied to the inlet section in a state where all of the reference solution in the inlet section has been transferred and the inlet section is empty, an air gap is formed between these solutions, so that a significant variation in the measurement result referred to as a so-called injection shock occurs. As a result, it becomes difficult to make a comparison in the trace amount of variation between the measurement result of the reference solution and the measurement result of the sample solution, so that the level of measurement precision cannot be ensured. Consequently a high level of proficiency is required for an operator in this type of operation.

Moreover, in general, in this type of measurement which uses a flow cell, a plurality of measurement devices are used and measurements are performed in parallel in some cases. Therefore the operation becomes complex and this creates a burden on the operator.

Furthermore, since the operation is complex, a series of measurements, in which a plurality of sample solutions are continuously measured, cannot be performed quickly and measurement intervals become long, so that workability is obstructed.

Moreover, there may be considered a method in which in a case where a reference solution is preliminarily accumulated and stored in the flow channel of a flow cell and a measurement is performed using this flow cell, first, a measurement of the reference solutions is performed, and then a sample solution is supplied to the flow cell, and measurement of the sample solution is performed. However, in this type of method, since a detecting section facing the flow channel is exposed to the reference solution for a prolonged period of time, the detecting section becomes deteriorated and this influences the measurement precision.

PRIOR ART DOCUMENTS

Patent Document

[Patent document 1] Japanese Unexamined Patent Application, First Publication No. 2002-148187

Non-Patent Document

[Non-patent document 1] Martin Zimmermann, Heinz Schmid, Patrick Hunziker and Emmanuel Delamarche, "Capillary pumps for autonomous capillary systems", The Royal Society of Chemistry 2007, Lab Chip, 2007, 7, p. 119-125, First published as an Advance Article on the web 17 Oct. 2006

SUMMARY OF THE INVENTION

Problem to be Solved by the Invention

The present invention takes into consideration the above circumstances, with an object of providing a flow cell and a liquid delivery method whereby the liquid delivery timing and the liquid delivery amount of a sample solution can be adjusted in accordance with an operation.

Moreover, an object of the present invention is to provide a flow cell and a liquid delivery method capable, with a simple configuration, of increasing the level of workability and ensuring the level of measurement precision.

Means for Solving the Problem (1) A flow cell according to one aspect of the present invention includes: a flow channel through which a sample solution flows; an inlet section which communicates with the flow channel and to which the sample solution is supplied; a transfer section which includes a plurality of opening sections, one end side of which communicates with the flow channel and an other side of which opens to outside air, and which communicates with the flow channel, and draws in and guides the sample solution supplied into the inlet section to the flow channel; a detecting section which faces the sample solution in the flow channel; and a sealing member which unsealably seals at least either one of the opening section or the inlet section.

According to this flow cell, the opening section on the other end side of the transfer section which draws in and guides the sample solution and to the flow channel, is sealed with the sealing member, and thereby the sample solution supplied to the inlet section does not flow to the flow channel until the sealing member has unsealed the opening section. Moreover, there are provided a plurality of the opening sections, and the amount of liquid delivery can be decided in accordance with the opening range of these opening sections. That is to say, the sample solution is transferred to a portion of the transfer section corresponding to the open opening section, and if this portion of the transfer section is filled with the sample solution, liquid delivery is stopped. Consequently the operator can freely adjust the liquid delivery timing and the liquid delivery amount of the sample solution supplied to the inlet section, in accordance with the operation.

According to this, in those cases where a solution such as a reference solution, which is different from the sample solution, needs to be flowed to the flow channel before or after the sample solution is supplied, the operator can actively decide the timing and amount of liquid delivery of the respective solutions. Therefore the following problems encountered heretofore will not occur. That is to say, there will not be a problem in that: the operator passively performs the operation with attention to the amount of decrease in the solution remaining in the inlet section; the next solution is supplied to the inlet section in a state where all of the solution supplied earlier has been transferred from the inlet section and the inlet section has become empty; there is formed an air gap between the solutions flowing through the flow channel; so that a significant variation in the measurement result referred to as a so-called injection shock occurs; and it becomes impossible to make a comparison in the trace amount of variation between the measurement result of the sample solution and the measurement result of the reference solution. Consequently a high level of proficiency is not required for the operator, and the operation can be performed simply, ensuring a sufficient level of measurement precision.

Moreover, even in those cases where a plurality of measurement devices are used and measurements are performed in parallel using a plurality of flow cells, the operator can freely adjust the liquid delivery timing in accordance with the operation. Therefore errors will not occur in the operation.

Furthermore, since the operation is not complex, a series of measurements, in which a plurality of sample solutions are continuously measured, can be performed more quickly and measurement intervals are reduced so that workability is improved.

(2) In the flow cell according to the one aspect of the present invention, the sealing member may be attached at least to either one of the opening section and the inlet section, and the sealing member may be detachable.

According to this flow cell, the sealing member is formed with an adhesive tape or the like, and the opening section can be simply opened by detaching this adhesive tape. Therefore workability is excellent and the opening range can be set at a high level of precision.

(3) In the flow cell according to the one aspect of the present invention, the sealing member may have a rod shape which blocks the opening section at a base end thereof, and a tip end thereof may be tilted to open the opening section.

According to this flow cell, the sealing member is formed with a rod-shaped polymer material for example, and the based end thereof blocks and seals the opening section. If the tip end of the sealing member is tilted, the opening section is opened so that the base end is detached or separated from the opening section in response to the tilt. That is to say, since the opening section can be opened by just tilting the tip end of the sealing member, workability is excellent.

(4) In the flow cell according to the one aspect of the present invention, the transfer section may include a plurality of through holes.

According to this flow cell, the transfer section includes a plurality of through holes, and in those cases where these through holes get wetted with a sample solution, the sample solution is drawn up from the flow channel by the so-called capillary action. Therefore the sample solution supplied to the inlet section is continuously drawn into the flow channel and supplied to the detecting section. Hence measurements can be performed at a high level of precision with a simple configuration without a large scale device configuration and complex operation as conventionally required, in which pressure from the outside of the flow cell is applied to the flow channel using a syringe pump or the like to make the sample solution flow, in order to continuously transfer the sample solution to the detecting section, and this syringe pump or the like needs to be cleaned and dried at each measurement.

(5) In the flow cell according to the one aspect of the present invention, the transfer section may include: a plurality of chambers, one end of which communicates with the flow channel and an other end of which is the opening section; and a plurality of columnar members arranged inside the chambers while having a clearance therebetween.

According to this flow cell, the intervals between the plurality of columnar members inside the chambers are configured so that capillary action is exerted, and the sample solution is drawn up from the flow channel. Therefore an effect similar to that of the flow cell described above can be achieved.

(6) The flow cell according to the one aspect of the present invention may include: a reserve section which causes the inlet section to accumulate the reference solution having properties approximate to those of the sample solution and used for measurement comparison, and which is unsealable, and the transfer section may include a first transfer section which communicates with an other end side of the flow channel, and draws in and guides the reference solution accumulated in the inlet section to the flow channel, and the accumulated reference solution may be delivered to the detecting section of the flow channel by unsealing the reserve section.

According to these flow cell and liquid delivery method, since there is provided the reserve section for accumulating the reference solution in the inlet section, the operator does not need to externally supply the reference solution to the flow cell at the time of measurement, and the accumulated reference solution can be delivered to the detecting section of the flow channel by performing a simple operation of unsealing the reserve section. Hence the sample solution only needs to be supplied to the flow cell at the time of measurement. Therefore there is no need for a complex device configuration in which a reference solution and a sample solution are respectively supplied to the flow cell using a plurality of syringe pumps, a liquid switch, a tube, and the like as practiced heretofore, so that the cost of equipment can be reduced. Moreover, there is no need for performing complex operations such as replacing, cleaning, and drying these syringe pumps, the liquid switch, the tube and the like at each measurement so that workability is improved.

Furthermore, since the amount the reference solution to be delivered is set to a predetermined amount preliminarily accumulated in the supplied section, there is no need for performing a complex operation as practiced heretofore in which the operator adjusts the amount of reference solution to be supplied to the flow cell at each measurement.

Moreover, even in those cases where a plurality of measurement devices are used and measurements are performed in parallel using a plurality of flow cells, the operator can simply perform liquid delivery in accordance with the operation. Therefore errors will not occur in the operation. Moreover, the operator can adjust the timing of liquid delivery in accordance with the operation and can flow the reference solution immediately before performing measurement. Therefore the detecting section of the flow channel is not exposed to the reference solution for a prolonged period of time so that the precision of measurement is increased.

(7) In the flow cell according to the one aspect of the present invention, there may be provided a second transfer section which communicates with the first transfer section and draws in the reference solution delivered to the flow channel, and which delivers the sample solution supplied to the inlet section, following the reference solution, to the detecting section of the flow channel.

According to this flow cell, after the first transfer section has delivered the reference solution to the detecting section, the second transfer section delivers the sample solution supplied to the inlet section to the detecting section of the flow channel, following the reference solution. Therefore there is no need for a complex device configuration in which pressure is applied to the flow channel from the outside of the flow cell, using a syringe pump and the like, to thereby deliver the reference solution and the sample solution, and the cost of equipment is reduced.

(8) In the flow cell according to the one aspect of the present invention, the inlet section may accumulate an amount of the reference solution, which partially remains in the inlet section, in an equilibrium state where the reference solution has been delivered to the flow channel and the liquid delivery has been stopped.

According to this flow cell, the amount of the reference solution to be accumulated in the inlet section is set so that it partially remains in the inlet section in an equilibrium state where the liquid delivery has been stopped. Therefore when supplying the sample solution following the reference solution, the following problems encountered heretofore will not occur. That is to say, there will not be a problem in that: the operator passively performs the operation with attention to the amount of decrease in the reference solution remaining in the inlet section; the sample solution is supplied to the inlet section in a state where all of the reference solution has been transferred from the inlet section and the inlet section has become empty; there is formed an air gap between the solutions flowing through the flow channel, so that a significant variation in the measurement result referred to as a so-called injection shock occurs; and it becomes impossible to make a comparison in the trace amount of variation between the measurement result of the sample solution and the measurement result of the reference solution.

That is to say, since the operator who has delivered the reference solution is able to supply the next sample solution to the flow cell and actively perform liquid delivery in accordance with the operation, a high level of proficiency is not required for the operator, and the operation can be performed simply, ensuring a sufficient level of measurement precision.

(9) In the flow cell according to the one aspect of the present invention, the reserve section may include a liquid sealed member having a closed container shape and connected to the inlet section, and the reference solution accumulated in the inlet section may be delivered to the detecting section by unsealing the liquid sealed member.

According to this flow cell, the reserve section includes a liquid sealed member, which is a closed container, such as an ampule or a micro-capsule, and the interior of this liquid sealed member communicates with the inlet section and accumulates the reference solution. Moreover, by unsealing the liquid sealed member, the outside air is drawn in from the unsealed portion and the reference solution accumulated in the inlet section is delivered to the detecting section of the flow channel. That is to say, since the reference solution can be flowed to the detecting section by just unsealing the liquid sealed member, workability is excellent.

(10) In the flow cell according to the one aspect of the present invention, the reserve section may include a sheet-shaped inlet section sealing member having a sheet shape and sealing an opening of the inlet section, and the reference solution accumulated in the inlet section may be delivered to the detecting section by unsealing the inlet section sealing member.

According to this flow cell, the reserve section includes a sheet-shaped inlet section sealing member such as an adhesive tape, and this inlet section sealing member is attached so as to seal the opening of the inlet section. Then if the inlet section sealing member is detached from the inlet section and is unsealed in accordance with the operation, the inlet section delivers the accumulated reference solution to the detecting section of the flow channel so as to draw in the outside air from the unsealed portion. Therefore, liquid delivery can be performed easily with a simple configuration, and the cost of manufacturing is reduced.

(11) In the flow cell according to the one aspect of the present invention, the first transfer section may include a first through hole, one end of which communicates with the flow channel and an other end of which opens to outside air, the reserve section may include a first sealing member which seals an opening of the first through hole, and the reference solution accumulated in the inlet section may be delivered to the detecting section by unsealing the first sealing member.

According to this flow cell, the reserve section includes the first sealing member such as an adhesive tape, and this first sealing member is attached so as to seal the opening of the first through hole. Then if the first sealing member is detached from the first through hole and is unsealed in accordance with the operation, the inlet section delivers the accumulated reference solution to the detecting section of the flow channel so as to draw in the outside air. Therefore, liquid delivery can be performed easily with a simple configuration, and the cost of manufacturing is reduced.

(12) In the flow cell according to the one aspect of the present invention, the second transfer section may include a second through hole, one end of which communicates with the first transfer section and an other end of which opens to outside air, there may be provided a second sealing member which seals an opening of the second through hole, and the sample solution supplied to the inlet section may be delivered to the detecting section by unsealing the second sealing member.

According to this flow cell, the second transfer section includes the second through hole and the opening of the second through hole is sealed by the second sealing member such as an adhesive tape. Therefore, the sample solution, which is supplied to the inlet section after the delivery of the reference solution, is not delivered to the flow channel and is accumulated in the inlet section until the second sealing member has been detached from the second through hole and has been unsealed. That is to say, by detaching the second sealing member from the second through hole and unsealing it, the inlet section delivers the accumulated sample solution to the detecting section of the flow channel so as to draw in the outside air. Consequently the timing of sample solution delivery can be actively controlled with a simple configuration, and the level of measurement precision can be increased, improving workability.

(13) In the flow cell according to the one aspect of the present invention, a sectional area of the flow channel in a region where the detecting section is provided may be smaller than a sectional area of the flow channel in a region where the detecting section is not provided.

(14) In the flow cell according to the one aspect of the present invention, an unsealing state of the sealing member may be controlled by an external device.

(15) A liquid delivery method for a flow cell according to one aspect of the present invention is a liquid delivery method for a flow cell in which a sample solution and a reference solution having properties approximate to those of the sample solution and used for comparing measurements are supplied to an inlet section individually, and a transfer section which communicates with the inlet section via a flow channel, draws in and guides the sample solution and the reference solution in the inlet section individually to the flow channel and delivers them to a detecting section facing the flow channel, and includes the steps of: supplying the reference solution to the inlet section, and drawing in the reference solution and flowing it to the detecting section by unsealing a part of the sealing member which seals a plurality of opening sections of the transfer section; and supplying the sample solution to the inlet section, and drawing in the sample solution and flowing it to the detecting section by unsealing a portion of the sealing members different from the part.

(16) A liquid delivery method for a flow cell according to one aspect of the present invention is a liquid delivery method for a flow cell in which a reference solution having properties approximate to those of a sample solution, and the sample solution are sequentially supplied to an inlet section which communicates with one end side of a flow channel and are guided to the flow channel, and are delivered to a detecting section facing the flow channel, and includes the steps of: causing a first transfer section which communicates with an other end side of the flow channel to draw in and deliver the reference solution to the detecting section of the flow channel by unsealing a reserve section for accumulating the reference solution in the inlet section; supplying the sample solution to the inlet section; and drawing in the reference solution delivered to the flow channel by a second transfer section which communicates with the first transfer section, and delivering the sample solution in the inlet section to the detecting section of the flow channel.

Effect of the Invention

According to the flow cell of the present invention, the liquid delivery timing and the liquid delivery amount of a sample solution can be adjusted in accordance with an operation. Therefore a high level of proficiency is not required for the operator, and measurements can be performed simply at a high level of precision so that workability is improved.

Moreover, according to the liquid delivery method for a flow cell of the present invention, the liquid delivery timing and the liquid delivery amount of the sample solution, and the liquid delivery timing and the liquid delivery amount of the reference solution can be adjusted in accordance with the operation. Therefore, the sample solution and the reference solution do not get mixed in the inlet section, and no air gap is formed between the sample solution and the reference solution flowing through the flow channel, so that the respective solutions can be delivered to the flow channel simply, giving a superior workability and improving the level of measurement precision.

Furthermore, according to the flow cell and the liquid delivery method of the present invention, there is provided the reserve section for accumulating a reference solution in the inlet section. Therefore the operator does not have to supply the reference solution to the inlet section every time when performing measurements, and the accumulated reference solution can be delivered to the detecting section of the flow channel by just unsealing the reserve section. Consequently the level of measurement workability can be increased with a simple configuration. Moreover, a predetermined amount of the reference solution preliminarily accumulated in the inlet section is delivered by unsealing the reserve section. Therefore the operator can actively control the liquid delivery timing and the liquid delivery amount, thereby increasing the level of measurement precision.

EMBODIMENTS FOR CARRYING OUT THE INVENTION

Hereunder, respective embodiments of the present invention are described, with reference to the drawings.

Figure 1:
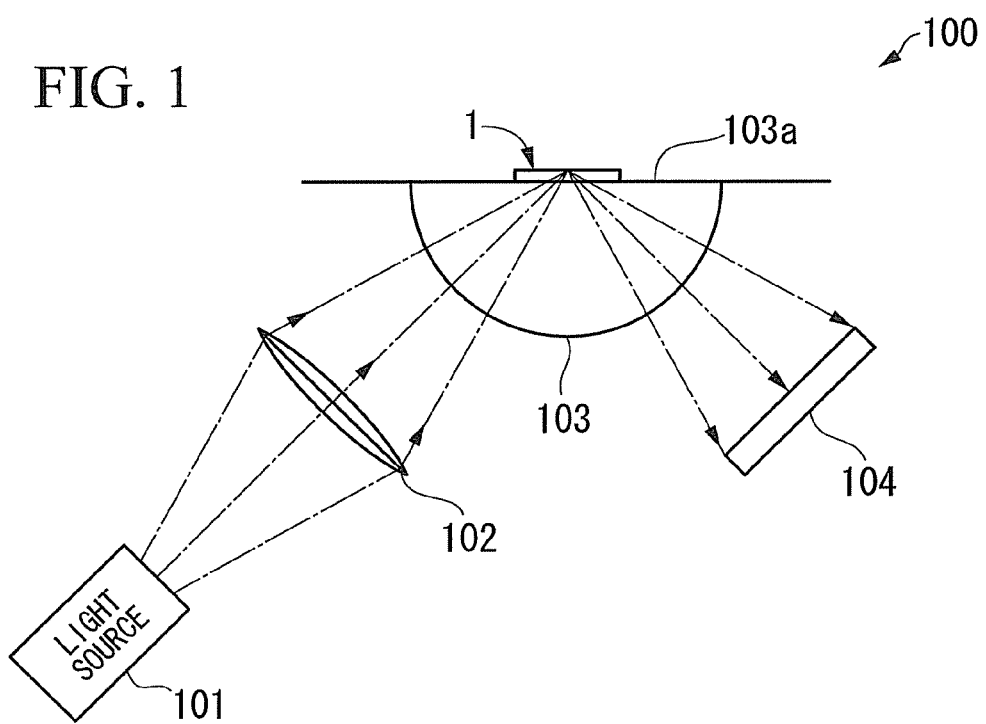
FIG. 1 is an explanatory diagram showing a schematic configuration of an SPR measurement device which uses a flow cell according to a first embodiment of the present invention.
Figure 2:
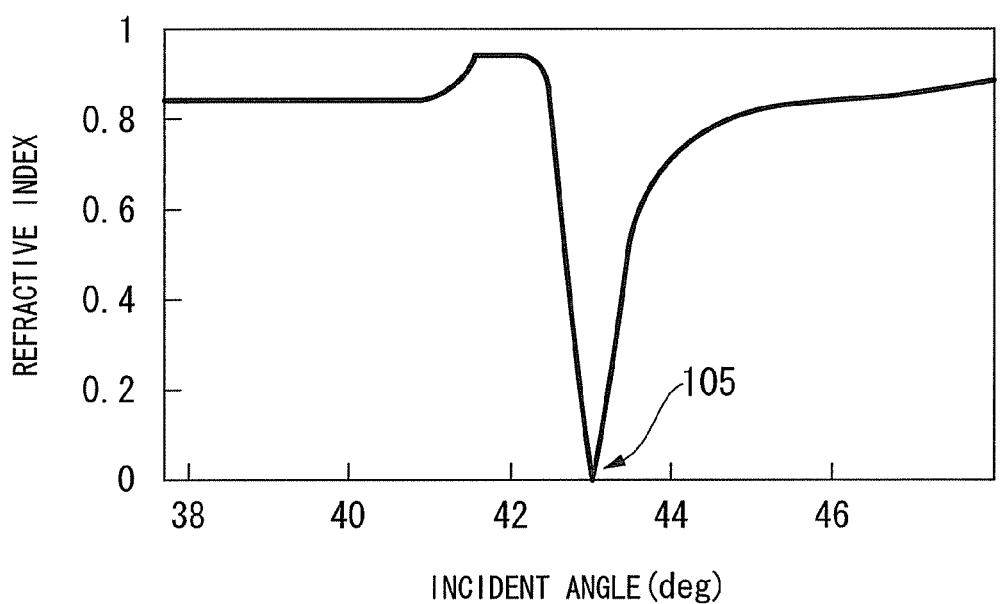
FIG. 2 is a characteristic diagram for describing a relationship between the reflectance and reflection angle of a detecting section measured with the SPR measurement device.
Figure 3:
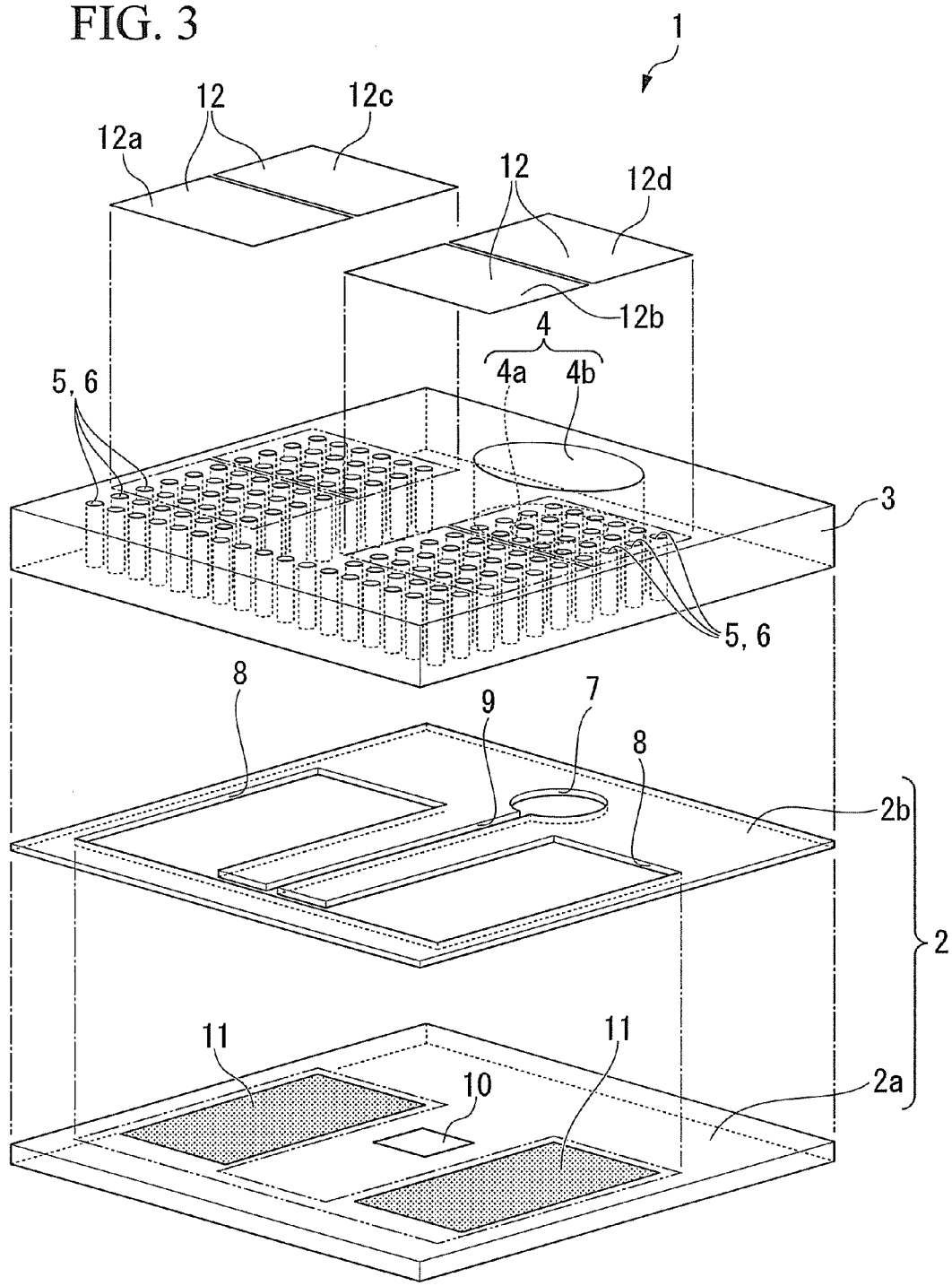
FIG. 3 is an exploded perspective view showing a schematic configuration of the flow cell according to the first embodiment of the present invention.
Figure 4:
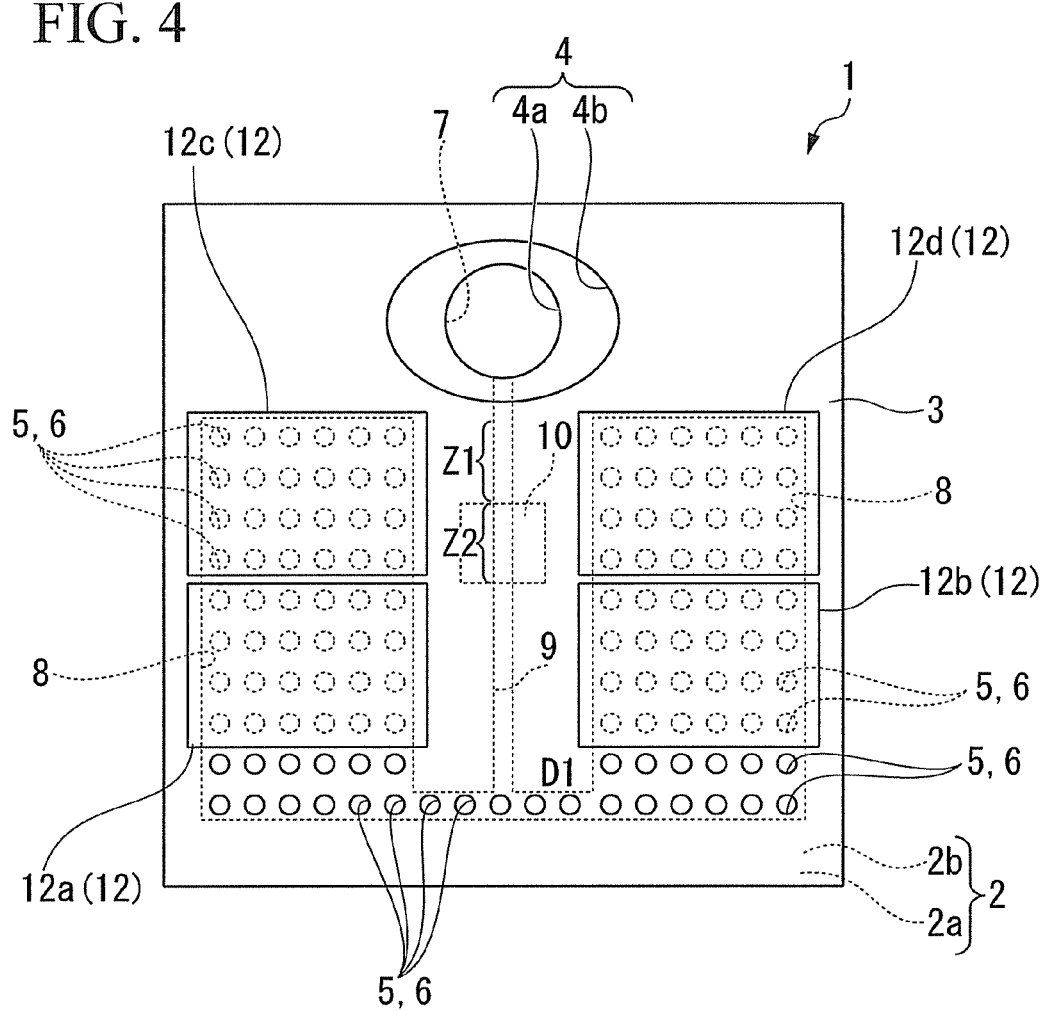
FIG. 4 is a plan view showing the schematic configuration of the flow cell according to the first embodiment of the present invention.

FIG. 1 is an explanatory diagram showing a schematic configuration of an SPR measurement device which uses a flow cell according to a first embodiment of the present invention. FIG. 2 is a characteristic diagram for describing a relationship between the reflectance and reflection angle of a detecting section measured with the SPR measurement device. FIG. 3 is an exploded perspective view showing a schematic configuration of the flow cell according to the first embodiment of the present invention. FIG. 4 is a plan view showing the schematic configuration of the flow cell according to the first embodiment of the present invention.

A flow cell 1 of the present embodiment is installed on an SPR measurement device 100, which uses a so-called surface plasmon resonance (SPR) phenomenon, which is resonance between evanescent waves and surface plasmon waves on the surface of a metallic thin film, with which a detection target test specimen (a DNA, antibody, or the like) comes in contact, and it is used for performing measurements.

As shown in FIG. 1, this SPR measurement device 100 is such that light emitted from a light source 101 is polarized by a polarizer (not shown in the diagram) to provide P-polarized light (hereunder, referred to as "incident light"). Next, the SPR measurement device 100 causes the strip-shaped incident light concentrated by a condensing lens 102 to irradiate on the curved surface side of a half-columnar prism 103. Then, the SPR measurement device 100 performs irradiation on a metallic thin film described later of the flow cell 1 which is adhered on a measurement surface 103a on the planar surface side of this prism 103. Moreover, the SPR measurement device 100 detects the reflected light with a light receiving section 104 including a CCD image sensor.

When the intensity (light intensity) of the reflected light detected by the light receiving section 104 is detected, then as shown in FIG. 2, the reflection intensity decreases at an angle (resonance angle), at which the above resonance occurs. Therefore a valley 105 where the reflectance is low is observed. The resonance angle is dependent on the optical characteristic (refractive index) of a sample solution which comes in contact with the metallic thin film. Therefore, by fixing an antibody on the metallic thin film and measuring the refractive index fluctuation caused by the bond between this antibody and an antigen, it is possible to perform a quantitative measurement of a specific substance.

As shown in FIG. 3 and FIG. 4, the flow cell 1 installed on the SPR measurement device 100 has a substantially rectangular solid outer shape or a substantially rectangular plate outer shape, and has a laminated structure. That is to say, in a state where the flow cell 1 is mounted on the SPR measurement device 100, there are provided a substantially rectangular plate-shaped lower substrate 2 arranged on the lower side, and an upper substrate 3 which is laminated on the upper side of the lower substrate 2 and the outer shape of which in plan view is formed in a shape substantially the same as that of the lower substrate 2. Moreover, for example, the plate thickness of the lower substrate 2 is approximately 1 mm, and the plate thickness of the upper substrate 3 is approximately 3 mM.

The upper substrate 3, on one end side of the substantially center (on the upper-right side in FIG. 3, or on the top side in FIG. 4) in the widthwise direction in a plan view thereof (in the upper-left to lower-right direction in FIG. 3, or in the left-right direction in FIG. 4), is provided with a substantially multistage columnar hole-shaped solution supply hole (inlet section) 4 for supplying each solution of a sample solution to be measured, a reference solution having properties (refractive index, viscosity, and the like) approximate to those of the sample solution, and a phosphate buffered saline (PBS) for cleaning purposes. The solution supply hole 4 has a columnar hole-shaped small diameter section 4a on the lower side, and an elliptic columnar hole-shaped large diameter section 4b having a diameter enlarged from that of the small diameter section 4a, formed on the upper side of the small diameter section 4a, and it passes through the upper substrate 3 in the plate thickness direction.

Moreover, in the upper substrate 3 there are provided a plurality of columnar hole-shaped through holes (transfer section) 5 and they pass through the upper substrate 3 in the plate thickness direction thereof. Furthermore, as shown in FIG. 4, these through holes 5 are arranged in a substantially rectangular shape in a plan view respectively on one side (on the left side in FIG. 4) and on the other side (on the right side in FIG. 4) in the widthwise direction. Moreover, these through holes 5 are linearly arranged so as to connect the end sections facing each other on the other end side (on the lower side in FIG. 4) of the respective planar rectangular shapes. These through holes 5 are set with an inner diameter of a range where a capillary action is exerted on the respective solutions, and the upper end thereof is of an opening section 6, which opens to the outside air while the lower end thereof communicates with a drawing flow channel 8 described later.

Furthermore, the lower substrate 2 is of a two-layer configuration, the lower side layer thereof is formed with a base substrate 2a made of a material, such as glass and acrylic polymer, which transmits light, and the upper side layer thereof is formed with a spacer section 2b made of a polymer film or the like.

The spacer section 2b has an opening portion formed therein so as to pass therethrough in the thickness direction. In this opening portion, in a position corresponding to the small diameter section 4a of the solution supply hole 4 of the upper substrate 3, there is formed a circular hole 7 having an inner diameter substantially the same as that of the small diameter section 4a. Moreover, in the spacer section 2b, there are provided the respective drawing flow channels 8 formed in a substantially rectangular-hole shape so as to correspond to the outer shape of the aforementioned plurality of through holes 5 arranged in a substantially rectangular shape in a plan view respectively on the one side and the other side in the widthwise direction of the upper substrate 3. The drawing flow channels 8 are set to an approximate height which does not form a clearance between the respective solutions and the through holes 5 thereabove when the respective solutions are supplied, and the height thereof in the plate thickness direction is approximately 10 to 100 μm for example.

Moreover, in the substantially widthwise center of the spacer section 2b there is formed a flow channel 9 which extends in a direction orthogonal to the widthwise direction. The flow channel 9 has an end section on one end side thereof communicated with the circular hole 7, and an end section on the other end side thereof branches to the one side and the other side in the widthwise direction so as to communicate with the respective drawing flow channels 8. Furthermore, the flow channel 9 is of a substantially sectional rectangular shape, and for example, the widthwise sectional dimension orthogonal to the extending direction thereof (hereunder, abbreviated as "sectional dimension") is approximately 1 mm, and the dimension in the plate thickness direction (height) is approximately 10 to 100 μm, and these are set within a range where capillary action is exerted on the respective solutions.

Moreover, in this manner, the circular hole 7 connected to the solution supply hole 4 and the drawing flow channels 8 connected to the through holes 5 communicate with each other through the flow channel 9.

Furthermore, in the substantially widthwise center of the upper surface of the base substrate 2a there is formed a rectangular metallic thin film (detecting section) 10. The metallic thin film 10 is, for example, made of Au (gold), and is arranged so as to be able to face and come in contact with the respective solutions flowing through the flow channel 9 of the spacer section 2b. Moreover, on the upper surface of the metallic thin film 10 there are arranged a plurality of antibodies (not shown in the diagram) along the flow channel 9. Although in the present embodiment, the metallic thin film 10 is arranged so as to correspond to a region in the substantially center on the upper surface of the base substrate 2a, which is used for measurement, the metallic thin film 10 may be formed broader and larger, exceeding the above region range.

Moreover, in a portion which corresponds to each of the drawing flow channels 8 of the spacer section 2b on the one side and on the other side in the width direction of the base substrate 2a, there is each formed a substantially rectangular surface active region 11. The surface active region 11 has undergone surface treatments, and it is set so that the wettability thereof with respect to the respective solutions differs from that of the region other than the surface active region 11.

That is to say, various types of surface treatments for the surface active region 11 are set to thereby vary and control the drawing state and flow rate of the respective solutions.

Moreover, on the upper surface of the upper substrate 3 there are attached a plurality of sealing members 12 formed with an adhesive tape. These sealing members 12 are arranged so as to oppose to the opening sections 6 of the through holes 5 of the upper substrate 3, and the respective sealing members 12 respectively seal the plurality of the opening sections 6.

As shown in FIG. 4, a plurality of the opening sections 6 arranged on the one end side on one side of the upper substrate 3 are sealed by a sealing member 12c. A plurality of the opening sections 6 arranged on the one end side on the other side of the upper substrate 3 are sealed by a sealing member 12d. Moreover, a plurality of the opening sections 6 arranged on the other end side of the sealing member 12c are sealed by a sealing member 12a. Further, a plurality of the opening sections 6 arranged on the other end side of the sealing member 12d are sealed by a sealing member 12b. These sealing members 12 can be detached respectively from the upper substrate 3.

Next, there is described a procedure of measuring a sample solution with the SPR measurement device 100, using the flow cell 1 configured in this manner.

First, the flow cell 1 is mounted, via matching oil or the like, on the measurement surface 103a of the prism 103 of the SPR measurement device 100. In a state where the flow cell 1 is mounted in this way, incident light from the light source 101 is irradiated on the metallic thin film 10 of the flow cell 1, and the reflected light is received by the light receiving section 104, creating a state where variations in refractive index can be measured.

Next, a PBS liquid is supplied to the solution supply hole 4 of the mounted flow cell 1. The supplied PBS liquid flows through the flow channel 9 as the flow channel 9 communicated with the solution supply hole 4 exerts a capillary action. Then, it is drawn in by the capillary action exerted as a result of the through holes 5 arranged in the vicinity of the end section of the other end side of the flow channel 9 and the through holes 5 arranged on the end section on the other end side of the respective drawing flow channels 8, getting wet.

In a state where all of the through holes 5 with the preliminarily opened opening sections 6 are filled with the PBS liquid, the sealing member 12a is detached to thereby open the plurality of the opening sections 6, which have been sealed by the sealing member 12a. As a result, the through holes 5 corresponding to the open opening sections 6 draw in the PBS liquid. When these through holes 5 are filled with the PBS liquid, the capillary action is no longer exerted. Consequently, the PBS liquid is no longer drawn in from the solution supply hole 4, and the liquid delivery stops. The amount of the PBS liquid to be supplied to the solution supply hole 4 is preliminarily set to an approximate amount, with which the solution remains in the small diameter section 4a of the solution supply hole 4, in this type of state where the liquid delivery is stopped.

Next, a reference solution is supplied to the solution supply hole 4 of the flow cell 1. The reference solution is prepared with a solution having properties approximate to those of the sample solution, and one which does not contain the test specimen of the sample solution to be measured is used. The sealing member 12b is detached in this type of state where the reference solution is accumulated in the solution supply hole 4, to thereby open the plurality of the opening sections 6 which have been sealed by the sealing member 12b. As a result, the reference solution starts to be drawn in due to the capillary action caused by the through holes 5 corresponding to the open opening sections 6 getting wetted with the remaining PBS liquid and the following reference solution, and the reference solution is continuously flowed to the metallic thin film 10 facing the flow channel 9. In this state, a first measurement of the reference solution is performed.

The reference solution which has flowed on the metallic thin film 10 is then drawn into the drawing flow channels 8, and then it is drawn into the open through holes 5. When these through holes 5 are filled with the reference solution, the capillary action is no longer exerted, and the reference solution is no longer drawn in from the solution supply hole 4, and the liquid delivery stops. The amount of the reference solution to be supplied to the solution supply hole 4 is preliminarily set to an approximate amount, with which the solution remains in the small diameter section 4a of the solution supply hole 4, in this type of state where the liquid delivery is stopped.

Next, a sample solution is supplied to the solution supply hole 4 of the flow cell 1. Then, the sealing member 12c is detached in the state where the sample solution is accumulated in the solution supply hole 4, to thereby open the plurality of the opening sections 6 which have been sealed by the sealing member 12c. As a result, the sample solution starts to be drawn in due to the capillary action caused by the through holes 5 corresponding to the open opening sections 6 getting wetted with the remaining reference solution and the following sample solution, and the sample solution is continuously flowed to the metallic thin film 10 facing the flow channel 9. In this state, a measurement of the sample solution is performed.

The sample solution which has flowed on the metallic thin film 10 is then drawn into the drawing flow channels 8, and then it is drawn into the open through holes 5. When these through holes 5 are filled with the sample solution, the capillary action is no longer exerted, and the sample solution is no longer drawn in from the solution supply hole 4, and the liquid delivery stops. The amount of the sample solution to be supplied to the solution supply hole 4 is preliminarily set to an approximate amount, with which the solution remains in the small diameter section 4a of the solution supply hole 4, in this type of state where the liquid delivery is stopped.

Next, the second reference solution is supplied to the solution supply hole 4 of the flow cell 1. The sealing member 12d is detached in the state where the reference solution is accumulated in the solution supply hole 4, to thereby open the plurality of the opening sections 6 which have been sealed by the sealing member 12d. As a result, the reference solution starts to be drawn in due to the capillary action caused by the through holes 5 corresponding to the open opening sections 6 getting wetted with the remaining sample solution and the following reference solution, and the reference solution is continuously flowed to the metallic thin film 10. In this state, a second measurement of the reference solution is performed.

The reference solution which has flowed on the metallic thin film 10 is then drawn into the drawing flow channels 8, and then it is drawn into the open through holes 5. When these through holes 5 are filled with the reference solution, the capillary action is no longer exerted, and the reference solution is no longer drawn in from the solution supply hole 4, and the liquid delivery stops.

Then, a measurement result of the sample solution is analyzed, using the first and second measurement results of the reference solution.

As described above, according to the flow cell 1 of the first embodiment, the opening sections 6 of the through holes 5, which draw in and guide the respective solutions of the sample solution, the reference solution, and the PBS liquid, are sealed by the sealing members 12. Therefore, in the state where the respective solutions are accumulated in the solution supply hole 4, the respective solutions do not flow into the flow channel 9 until the sealing members 12 have opened the opening sections 6. Moreover, the respective sealing members 12a to 12d seal the respective opening sections 6, and it is consequently possible to decide the liquid delivery amount of the respective solutions according to the range where these sealing members 12a to 12d are detached to open the opening sections 6.

That is to say, the respective solutions are only transferred to the through holes 5 corresponding to the respective opening sections 6 opened by the respective sealing members 12a to 12d, and the liquid delivery stops when these through holes 5 are filled with the solution. Consequently the operator can freely adjust the liquid delivery timing and the liquid delivery amount of the respective solutions supplied to the solution supply hole 4, in accordance with the operation.

Thus, the operator can actively decide the timing and amount of liquid delivery of the respective solutions. Therefore, there will not be the situation encountered heretofore where the operator passively performs an operation with attention to the amount of decrease in the respective solutions remaining in the solution supply hole 4, the next solution is supplied to the solution supply hole 4 in a state where all of the solution supplied earlier has been transferred from the solution supply hole 4 and the solution supply hole 4 has become empty, and there is formed an air gap between the solutions flowing through the flow channel 9, so that a significant variation in measurement results referred to as a so-called injection shock occurs. Therefore, there will not be a situation where it becomes impossible to make a comparison in the trace amount of variation between the measurement result of the sample solution and the measurement result of the reference solution. Consequently a high level of proficiency is not required for the operator, and the operation can be performed simply, ensuring a sufficient level of measurement precision.

Moreover, even in those cases where a plurality of the SPR measurement devices 100 are used and measurements are performed in parallel using a plurality of the flow cells 1, the operator can freely adjust the liquid delivery timing in accordance with the operation. Therefore errors will not occur in the operation.

Furthermore, since the operation is not complex, a series of measurements, in which a plurality of sample solutions are continuously measured, can be performed more quickly and measurement intervals are reduced so that workability is improved.

Moreover, since the sealing members 12 are formed with an adhesive tape and the opening sections 6 can be unsealed simply by detaching the adhesive tape, a high level of workability can be achieved, and further, the range of opening can be set at a high level of precision.

Furthermore, since the plurality of through holes 5 draw up the respective solutions from the flow channel 9 by so-called capillary action, the respective solutions supplied to the solution supply hole 4 are continuously drawn into the flow channel 9 and supplied to the metallic thin film 10. Hence measurements can be performed at a high level of precision with a simple configuration without a large scale device configuration and complex operation as conventionally required, in which pressure from the outside of the flow cell 1 is applied to the flow channel 9 using a syringe pump or the like to make the respective solutions flow, in order to continuously transfer the respective solutions to the metallic thin film 10, and this syringe pump or the like needs to be cleaned and dried at each measurement.

Next, a second embodiment of the present invention is described, with reference to FIG. 5 to FIG. 8.

Figure 5:
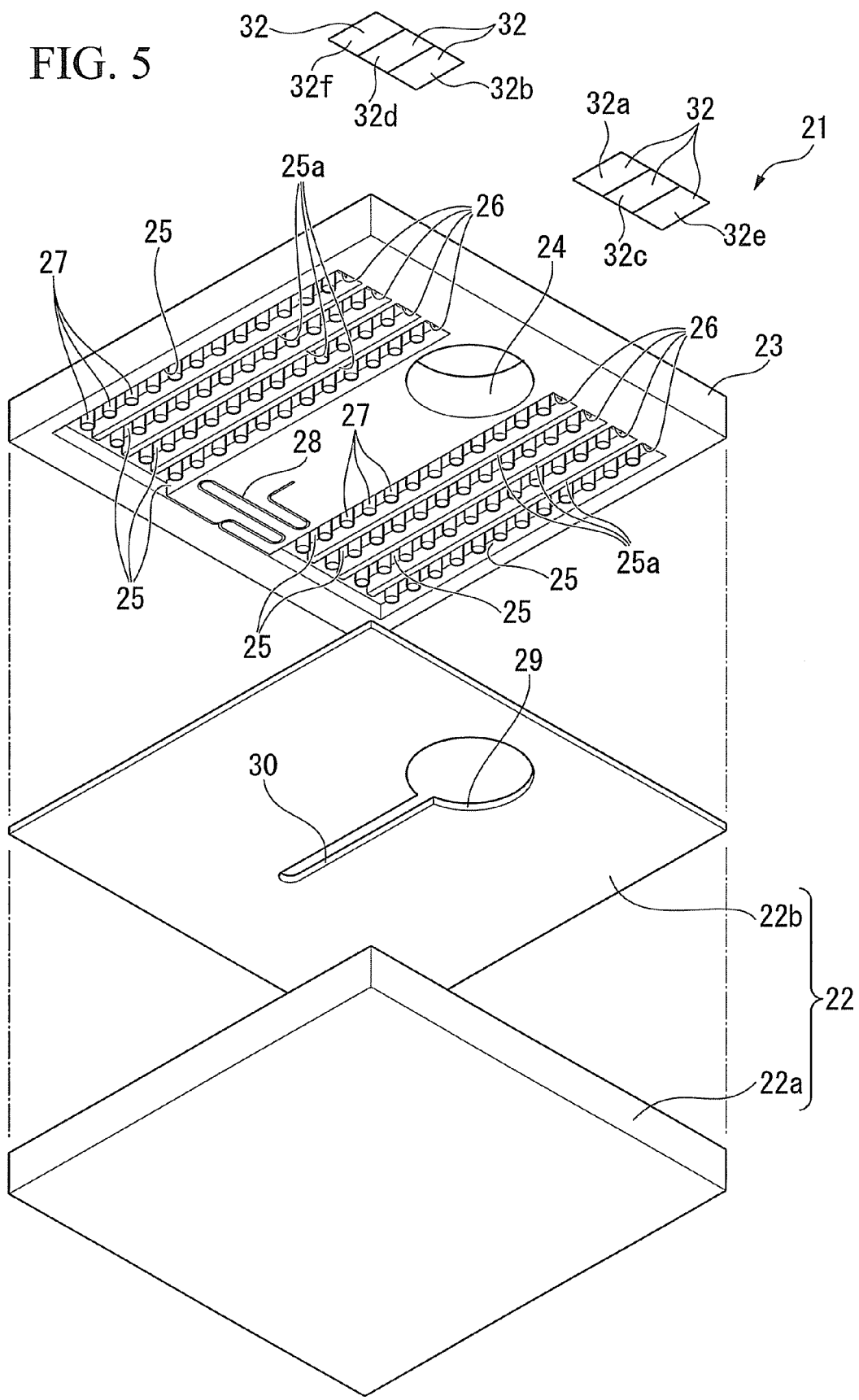
FIG. 5 is an exploded perspective view showing a schematic configuration of a flow cell according to a second embodiment of the present invention.
Figure 6:
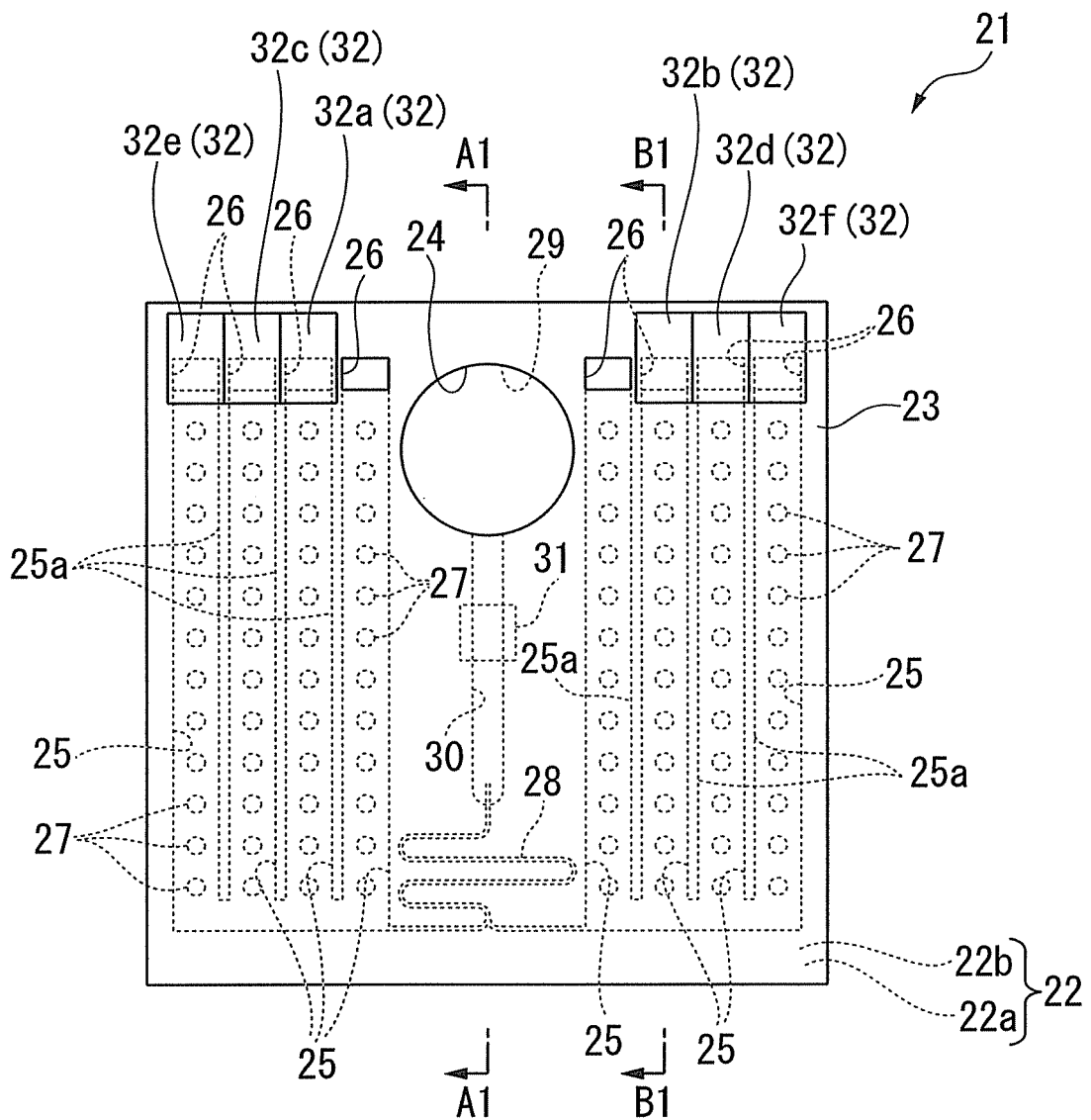
FIG. 6 is a plan view showing the schematic configuration of the flow cell according to the second embodiment of the present invention.
Figure 7:
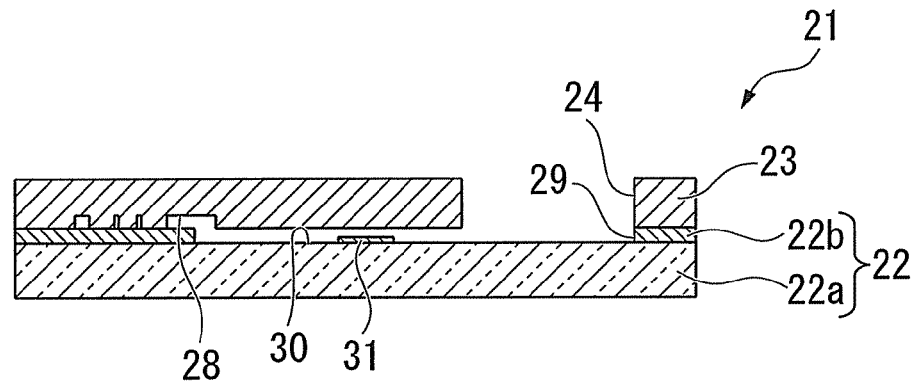
FIG. 7 is a sectional side view taken along the line A1-A1 in FIG. 6.
Figure 8:
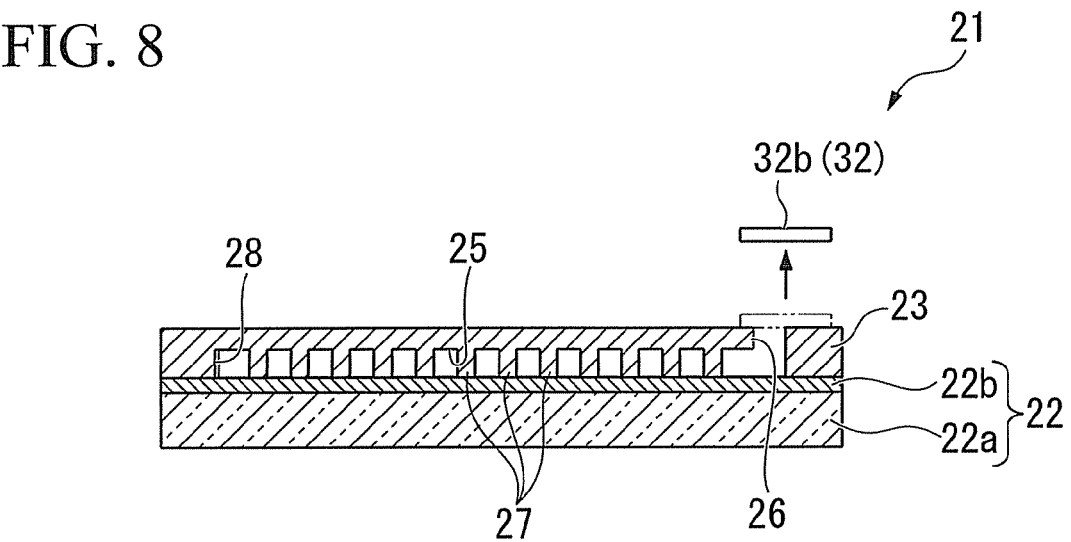
FIG. 8 is a sectional side view taken along the line B1-B1 in FIG. 6.

FIG. 5 is an exploded perspective view showing a schematic configuration of a flow cell according to the second embodiment of the present invention. FIG. 6 is a plan view showing the schematic configuration of the flow cell according to the second embodiment of the present invention. FIG. 7 is a sectional side view taken along the line A1-A1 in FIG. 6. FIG. 8 is a sectional side view taken along the line B1-B1 in FIG. 6.

Members the same as those in the first embodiment described above are denoted by the same reference symbols, and descriptions thereof are omitted.

An upper substrate 23 of a flow cell 21 of the second embodiment, on one end side of the substantially center (on the upper-right side in FIG. 5, or on the top side in FIG. 6) in the widthwise direction in a plan view thereof (in the upper-left to lower-right direction in FIG. 5, or in the left-right direction in FIG. 6), is provided with a columnar hole-shaped solution supply hole (inlet section) 24 for supplying respective solutions. The solution supply hole 24 passes through the upper substrate 23 in the plate thickness direction thereof.

Moreover, in the upper substrate 23, on one side (on the lower-right side in FIG. 5 or on the left side in FIG. 6) and on the other side (on the upper-left side in FIG. 5 or on the right side in FIG. 6) in the widthwise direction thereof, there are formed a plurality of rectangular recess groove-shaped chambers (transfer section) 25 which respectively open toward the lower surface side in the plate thickness direction. These chambers 25 are formed so as to extend in a direction orthogonal to the widthwise direction, and the adjacent chambers 25 are separated from each other by wall sections 25a.

Moreover, on the end section on one end side of the chamber 25, there is formed a substantially rectangular columnar hole-shaped opening section 26 which passes through the upper substrate 23 in the plate thickness direction. A plurality of the opening sections 26 are provided so as to correspond to the respective chambers 25, and its upper end portion in the plate thickness direction is open to the outside air. Furthermore, the end sections on the other end side of the plurality of chambers 25 arranged on the one side (on the lower-left side in FIG. 5 or on the lower side in FIG. 6), communicate with each other. Moreover, the end sections on the other end side of the plurality of chambers 25 arranged on the other side also communicate with each other.

Furthermore, in the respective chambers 25, there are provided a plurality of substantially cylindrical columnar members (transfer section) 27 so as to suspend from the ceiling portion, which is the bottom surface. These columnar members 27 are arranged inside the chamber 25 with a clearance between each other, and are linearly arranged in a direction orthogonal to the widthwise direction. Moreover, between the outer circumference of the columnar member 27 and the adjacent wall section 25a, there is provided a slight clearance. The clearance inside the respective chambers 25 is set to a dimension within a range where capillary action is exerted on the respective solutions.

Moreover, on the other end side of the substantially widthwise center of the upper substrate 23, there is formed a meandering recess groove-shaped meandering flow channel 28 which opens toward the lower surface side in the plate thickness direction. The meandering flow channel 28 is formed in a crank shape or wave shape which turns back a plurality of number of times to the widthwise one side and to the other side, and the respective turning-back portions are formed in a smooth curved line shape.

Moreover, the end section on the other end side of the meandering flow channel 28 branches towards the widthwise one side and to the other side. They communicate respectively with the end section on the other end side of the chamber 25 arranged widthwise inward on one side, and with the end section on the other end side of the chamber 25 arranged widthwise inward on the other side. Moreover, the end section on one end side of the meandering flow channel 28 is arranged in the substantially center of the upper substrate 23, and communicates with a flow channel 30 described later. Furthermore, the sectional dimension of the meandering flow channel 28 is set to a dimension in a range where capillary action is exerted on the respective solutions.

Furthermore, the lower substrate 22 is of a two-layer configuration, the lower side layer thereof is formed with a base substrate 22a made of a material, such as glass and acrylic polymer, which transmits light, and the upper side layer thereof is formed with a spacer section 22b made of a polymer film or the like.

The spacer section 22b has an opening portion formed therein so as to pass therethrough in the thickness direction. In this opening portion, in a position corresponding to the solution supply hole 24 of the upper substrate 23, there is formed a circular hole 29 having an inner diameter substantially the same as that of the solution supply hole 24. Moreover, in the substantially widthwise center of the spacer section 22b, there is formed a flow channel 30 which extends in a direction orthogonal to the widthwise direction.

The flow channel 30 has an end section on one end side thereof communicating with the circular hole 29, and an end section on the other end side thereof communicating with the end section on one end side of the meandering flow channel 28 of the spacer section 22b. Furthermore, the flow channel 30 is of a substantially sectional rectangular shape, and for example, the widthwise sectional dimension thereof is approximately 1 mm, and the dimension in the plate thickness direction (height) is approximately 10 to 100 µm, and these are set within a range where capillary action is exerted on the respective solutions.

Moreover, in this manner, the circular hole 29 connected to the solution supply hole 24 and the meandering flow channel 28 connected to the chamber 25 communicate with each other through the flow channel 30.

Furthermore, in the substantially widthwise center of the upper surface of the base substrate 22a, there is formed a rectangular metallic thin film (detecting section) 31. On the metallic thin film 31, there is applied an antibody. The metallic thin film 31 and the antibody are arranged so as to be able to face and come in contact with the respective solutions flowing through the flow channel 30 of the spacer section 22b.

Moreover, on the upper surface of the upper substrate 23, there are attached a plurality of sealing members 32 formed with an adhesive tape. These sealing members 32 are arranged respectively opposed to the opening sections 26 of the upper substrate 23, and seal the opening sections 26.

As shown in FIG. 6, among a plurality of the opening sections 26 arranged on one side of the upper substrate 23, only the opening section 26 which is arranged widthwise inward is in an open state, and other opening sections 26 are respectively sealed by sealing members 32a, 32c, and 32e. Moreover, among a plurality of the opening sections 26 arranged on the other side of the upper substrate 23, only the opening section 26 which is arranged widthwise inward is in an open state, and other opening sections 26 are respectively sealed by sealing members 32b, 32d, and 32f. These sealing members 32 can be detached respectively from the upper substrate 23.

A sample solution is measured with the SPR measurement device 100, using the flow cell 21 with this type of configuration. First, the flow cell 21 is mounted, via matching oil or the like, on the measurement surface 103a of the prism 103 of the SPR measurement device 100, creating a state where variations in refractive index can be measured.

Next, a PBS liquid is supplied to the solution supply hole 24 of the mounted flow cell 21. The supplied PBS liquid flows through the flow channel 30 as the flow channel 30 communicated with the solution supply hole 24 exerts a capillary action. The PBS liquid is then drawn into the meandering flow channel 28 which communicates with the end section on the other end side of the flow channel 30, and is drawn into the chambers 25 arranged widthwise inward respectively on one side and on the other side of the upper substrate 23. The PBS liquid drawn into the respective widthwise inward chambers 25 flows inside as the capillary action is exerted due to the respective chambers 25 getting wetted with the PBS liquid, and is then guided to the respective opening sections 26 on one end side of these chambers 25. When the PBS liquid has been delivered to the opening sections 26 and the respective chambers 25 are filled therewith in this way, the capillary action is no longer exerted and the liquid delivery stops.

If the sealing member 32a is detached and the opening section 26, which has been sealed by this sealing member 32a, is opened in a state where the PBS liquid is supplied to the respective chambers 25 arranged widthwise inward, the chamber 25 corresponding to the open opening section 26 draw in the PBS liquid. When the chamber 25 is filled with the PBS liquid, the capillary action is no longer exerted, and the PBS liquid is no longer drawn in from the solution supply hole 24, and the liquid delivery stops. The amount of the PBS liquid to be supplied to the solution supply hole 24 is preliminarily set to an approximate amount, with which the solution remains slightly in the solution supply hole 24, in this type of state where the liquid delivery is stopped.

Next, a reference solution is supplied to the solution supply hole 24 of the flow cell 21. The sealing member 32b is detached in the state where the reference solution is accumulated in the solution supply hole 24, to thereby open the opening section 26 which has been sealed by the sealing member 32b. As a result, the reference solution starts to be drawn in due to the capillary action caused by the chamber 25 corresponding to the open opening section 26 getting wetted with the remaining PBS liquid and the following reference solution, and the reference solution is continuously flowed to the metallic thin film 31 facing the flow channel 30. In this state, a first measurement of the reference solution is performed.

The reference solution which has flowed on the metallic thin film 31 is then drawn into the meandering flow channel 28, and then it is drawn into the chamber 25 corresponding to the open opening section 26. When the chamber 25 is filled with the reference solution, the capillary action is no longer exerted, and, the reference solution is no longer drawn in from the solution supply hole 24, and the liquid delivery stops. The amount of the reference solution to be supplied to the solution supply hole 24 is preliminarily set to an approximate amount, with which the solution remains slightly in the solution supply hole 24, in this type of state where the liquid delivery is stopped.

Next, a sample solution is supplied to the solution supply hole 24 of the flow cell 21. Then, the sealing member 32c is detached in the state where the sample solution is accumulated in the solution supply hole 24, to thereby open the opening section 26 which has been sealed by the sealing member 32c. As a result, the sample solution starts to be drawn in due to the capillary action caused by the chamber 25 corresponding to the open opening section 26 getting wetted with the remaining reference solution and the following sample solution, and the sample solution is continuously flowed to the metallic thin film 31 on the flow channel 30. In this state, a measurement of the sample solution is performed.

The sample solution which has flowed on the metallic thin film 31 is drawn into the meandering flow channel 28, and it is drawn into the chamber 25 with the open opening section 26. When these chamber 25 is filled with the sample solution, the sample solution is no longer drawn in from the solution supply hole 24, and the liquid delivery stops. The amount of the sample solution to be supplied to the solution supply hole 24 is preliminarily set to an approximate amount, with which the solution remains slightly in the solution supply hole 24, in this type of state where the liquid delivery is stopped.

Next, the second reference solution is supplied to the solution supply hole 24 of the flow cell 21. The sealing member 32d is detached in the state where the reference solution is accumulated in the solution supply hole 24, to thereby open the opening section 26 which has been sealed by the sealing member 32d. As a result, the reference solution starts to be drawn in due to the capillary action caused by the chamber 25 corresponding to the open opening section 26 getting wetted with the remaining sample solution and the following reference solution, and the reference solution is continuously flowed to the metallic thin film 31. In this state, a second measurement of the reference solution is performed.

The reference solution which has flowed on the metallic thin film 31 is drawn into the meandering flow channel 28, and then it is drawn into the chamber 25 having the open opening section 26. When the chamber 25 is filled with the reference solution, the reference solution is no longer drawn in from the solution supply hole 24, and the liquid delivery stops.

Then, a measurement result of the sample solution is analyzed, using the first and second measurement results of the reference solution.

Here, third and fourth reference solutions may be further flowed to the metallic thin film 31 to perform respective measurements, using the sealing members 32e and 32f. If the measurement result of the sample solution is analyzed with use of the measurement results of the first to fourth reference solutions, it is possible to perform measurement at a higher level of precision.

As described above, according to the flow cell 21 of the second embodiment, there are provided a plurality of the chambers 25, with which the capillary action can be exerted, and the respective chambers 25 have the opening sections 26. The respective sealing members 32 corresponding to these opening sections 26 are detached to open the opening sections 26, and thereby the respective solutions are drawn up from the flow channel 30 and are supplied to the metallic thin film 31. The liquid delivery stops when the chambers 25 corresponding to the open opening sections 26 are filled with the respective solutions, and consequently an effect similar to that of the first embodiment described above can be achieved.

Figure 9:
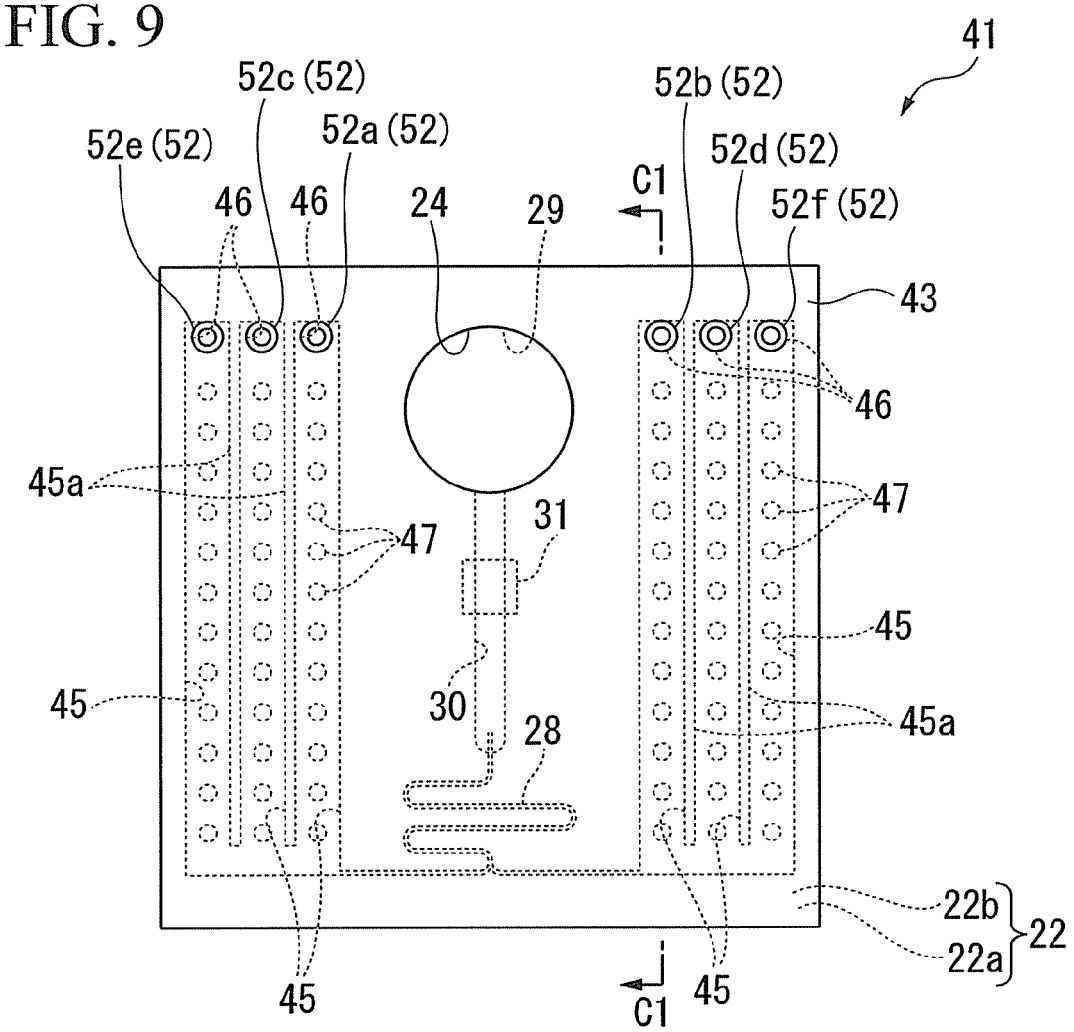
FIG. 9 is a plan view showing a schematic configuration of a flow cell according to a third embodiment of the present invention.
Figure 10:
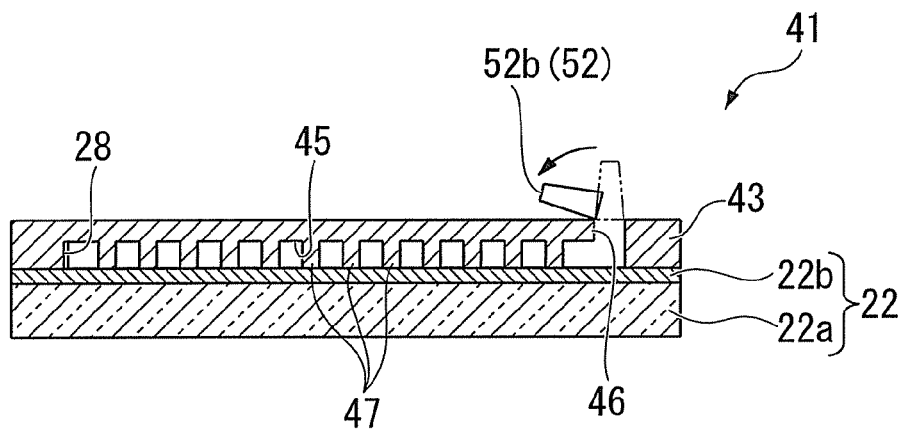
FIG. 10 is a sectional side view taken along the line C1-C1 in FIG. 9.

Next, a third embodiment of the present invention is described, with reference to FIG. 9 and FIG. 10.

FIG. 9 is a plan view showing a schematic configuration of a flow cell according to the third embodiment of the present invention. FIG. 10 is a sectional side view taken along the line C1-C1 in FIG. 9.

Members the same as those in the first and second embodiments described above are denoted by the same reference symbols, and descriptions thereof are omitted.

An upper substrate 43 of a flow cell 41 of the third embodiment is formed with a polymer material or the like. On one side (on the left side in FIG. 9) and on the other side (on the right side in FIG. 9) in the widthwise direction in a plan view of the flow cell 41 (the left-right direction in FIG. 9), there are respectively provided a plurality of rectangular recess groove-shaped chambers (transfer section) 45 which open toward the lower surface side in the plate thickness direction. These chambers 45 are formed so as to extend in a direction orthogonal to the widthwise direction, and the adjacent chambers 45 are separated from each other by wall sections 45a.

Moreover, in the end section on one end side (on the top side in FIG. 9) of the chamber 45, there is formed a substantially cylindrical hole-shaped concave section (opening section) 46 which opens toward the lower surface side in the plate thickness direction. The concave section 46 is provided in a plurality of positions corresponding to the respective chambers 45, and the upper end portion in the plate thickness direction, which is the bottom surface thereof, is integrated to the base end section of a sealing member 52 formed with a polymer material or the like in a substantially round bar shape or a truncated conical shape, and is sealed.

Furthermore, in the respective chambers 45, there are provided a plurality of substantially cylindrical columnar members (transfer section) 47 suspended therefrom. These columnar members 47 are arranged inside the chamber 45 with a clearance between each other, and are linearly arranged in a direction orthogonal to the widthwise direction. Moreover, between the outer circumference of the columnar member 47 and the adjacent wall section 45a, there is provided a slight clearance. The clearance inside the respective chambers 45 is set to a dimension within a range where capillary action is exerted on the respective solutions.

A sample solution is measured with the SPR measurement device 100, using the flow cell 41 with this type of configuration. First, the flow cell 41 is mounted, via matching oil or the like, on the measurement surface 103a of the prism 103 of the SPR measurement device 100, creating a state where variations in refractive index can be measured.

Next, a PBS liquid is supplied to the solution supply hole 24 of the mounted flow cell 41. Here, the supplied PBS liquid is not delivered to the flow channel 30 and is in a state of being accumulated in the solution supply hole 24. Next, among the sealing members 52, the tip end portion of the sealing member 52a arranged widthwise inward on one side is tilted as shown in FIG. 10. Next, the base end portion is separated from the concave section 46 so as to open the concave section 46, which has been sealed at the base end portion, to the outside air.

When the concave section 46 is opened, the PBS liquid is drawn in due to the capillary action caused by the chamber 45, which corresponds to this concave section 46 opened by the sealing member 52a, getting wetted with the PBS liquid. When the chamber 45 is filled with the PBS liquid, the capillary action is no longer exerted, and the PBS liquid is no longer drawn in from the solution supply hole 24, and the liquid delivery stops. The amount of the PBS liquid to be supplied to the solution supply hole 24 is preliminarily set to an approximate amount, with which the solution remains slightly in the solution supply hole 24, in this type of state where the liquid delivery is stopped.

Next, a reference solution is supplied to the solution supply hole 24 of the flow cell 41. In the state where the reference solution is accumulated in the solution supply hole 24, the tip end portion of the sealing member 52b arranged widthwise inward on the other side is tilted. Then the base end portion thereof is separated from the concave section 46 so as to open the concave section 46, which has been sealed at the base end portion, to the outside air.

When the concave section 46 is opened, the reference solution starts to be drawn in due to the capillary action caused by the chamber 45, which corresponds to this concave section 46 opened by the sealing member 52b, getting wetted with the remaining PBS liquid and the following reference solution. As a result, the reference solution is continuously flowed to the metallic thin film 31 facing the flow channel 30. In this state, a first measurement of the reference solution is performed.

When this chamber 45 is filled with the reference solution, the capillary action is no longer exerted. Consequently, the reference solution is no longer drawn in from the solution supply hole 24, and the liquid delivery stops. The amount of the reference solution to be supplied to the solution supply hole 24 is preliminarily set to an approximate amount, with which the solution remains slightly in the solution supply hole 24, in this type of state where the liquid delivery is stopped.

Next, a sample solution is supplied to the solution supply hole 24 of the flow cell 41. In the state where the sample solution is accumulated in the solution supply hole 24, the tip end portion of the sealing member 52c adjacent to one side of the sealing member 52a is tilted and the base end portion thereof is separated from the concave section 46, to thereby open the concave section 46, which has been sealed by this base end portion, to the outside air.

When the concave section 46 is opened, the sample solution starts to be drawn in due to the capillary action caused by the chamber 45, which corresponds to this concave section 46 opened by the sealing member 52c, getting wetted with the remaining reference solution and the following sample solution. As a result, the sample solution is continuously flowed to the metallic thin film 31 facing the flow channel 30. In this state, a measurement of the sample solution is performed.

When this chamber 45 is filled with the sample solution, the capillary action is no longer exerted. Consequently, the sample solution is no longer drawn in from the solution supply hole 24, and the liquid delivery stops. The amount of the sample solution to be supplied to the solution supply hole 24 is preliminarily set to an approximate amount, with which the solution remains slightly in the solution supply hole 24, in this type of state where the liquid delivery is stopped.

Next, the second reference solution is supplied to the solution supply hole 24 of the flow cell 41. In the state where the reference solution is accumulated in the solution supply hole 24, the tip end portion of the sealing member 52d adjacent to the other side of the sealing member 52b is tilted and the base end portion thereof is separated from the concave section 46. As a result, the concave section 46, which as been sealed by this base end portion, is opened to the outside air.

When the concave section 46 is opened, the reference solution starts to be drawn in due to the capillary action caused by the chamber 45, which corresponds to this concave section 46 opened by the sealing member 52d, getting wetted with the remaining sample solution and the following reference solution. As a result, the reference solution is continuously flowed to the metallic thin film 31 facing the flow channel 30. In this state, a second measurement of the reference solution is performed.

When this chamber 45 is filled with the reference solution, the capillary action is no longer exerted, and the reference solution is no longer drawn in from the solution supply hole 24, and the liquid delivery stops.

Then, a measurement result of the sample solution is analyzed, using the first and second measurement results of the reference solution.

Here, third and fourth reference solutions may be further flowed to the metallic thin film 31 to perform respective measurements, using the sealing members 52e and 52f. If the measurement result of the sample solution is analyzed with use of the measurement results of the first to fourth reference solutions, it is possible to perform measurement at a higher level of precision.

As described above, according to the flow cell 41 of the third embodiment, the sealing member 52 is formed with a polymer material or the like in a substantially round bar shape, and the base end portion thereof blocks and thereby seals the concave section 46. Further, when the tip end portion of the sealing member 52 is tilted, in response to this tilting, the base end portion opens the concave section 46 so as to be separated from the concave section 46. That is to say, since the concave section 46 can be unsealed by just tilting the tip end portion of the sealing member 52, workability is excellent.

The present invention is not limited to the aforementioned embodiments, and various types of modifications may be made thereto without departing from the scope of the invention.

For example, the order of opening the opening sections 6 and 26, and the concave section 46 is not limited to that in the first to third embodiments, and it may be appropriately changed in consideration of workability for the operator.

Moreover, the shape, number, and arrangement of the opening sections 6 and 26, and the concave section 46, may be appropriately set according to various types of measurements.

Furthermore, the present embodiments describe the case where the sealing members 12 and 32 are an adhesive tape attached on the opening sections 6 and 26, and the sealing member 52 is formed with a polymer material or the like which blocks the concave section 46. However, it is not limited to this as long as it is of a configuration capable of unsealing the sealed opening sections 6 and 26, and the concave section 46 so as to open to the outside air. For example, the configuration may be such that in the state where the flow cells 1, 21, and 41 are mounted on the SPR measurement device 100, these opening sections 6 and 26, and the concave section 46 are mechanically blocked with a sealing member formed with a movable arm, a clamp plate or the like preliminarily installed on the SPR measurement device 100, and they are sequentially unsealed according to the liquid delivery timing of the respective solutions.

Moreover, the present embodiments describe the case where the through hole 5, the chambers 25 and 45, and the columnar members 27 and 47 are a transfer section which draws in and guides the respective solutions to the flow channels 9 and 30. However, they are not limited to these, and for example, they may be configured with a flow channel, a cavity or the like which exerts the capillary action to thereby draw in the respective solutions.

Furthermore, the shape, number, and arrangement of the through hole 5, the chambers 25 and 45, and the columnar members 27 and 47 are not limited to those in the present embodiments.

Moreover, the present embodiments describe the case where the flow cell is used with the SPR measurement device 100. However, it may be applied to other devices in which sample solutions are flowed and measured. That is to say, an application may be made in areas where sample solutions are handled such as with micro TAS, Lab on a chip, micro combinatorial chemistry, chemical IC, chemical sensors, biosensors, microanalysis, electrochemical analysis, chromatography, QCM measurement, and ATR measurement.

Next, a fourth embodiment of the present invention is described.

Figure 11:
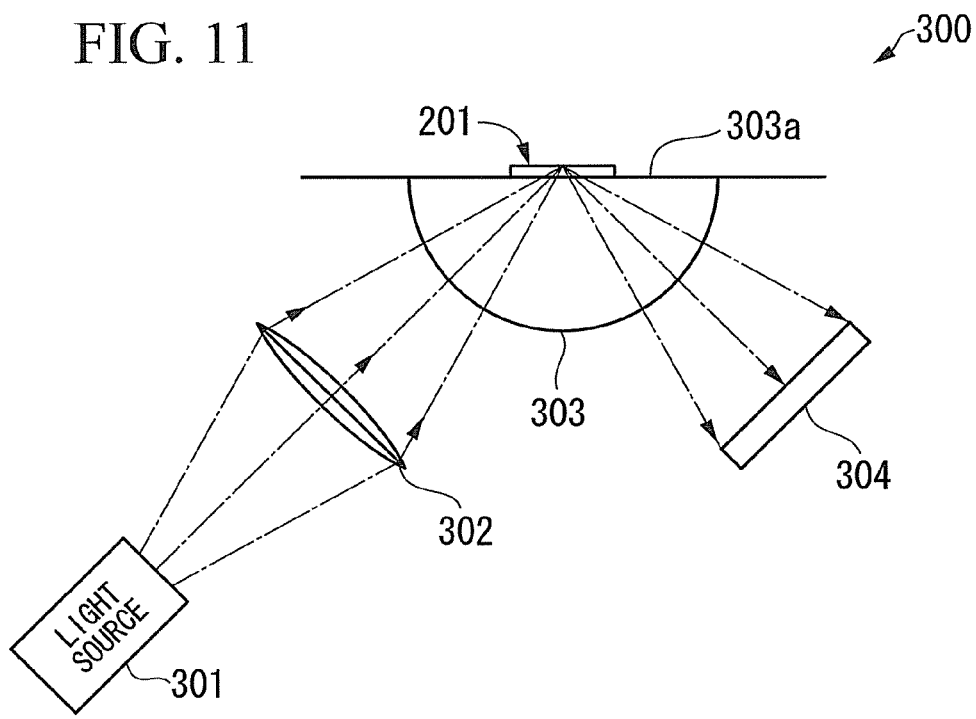
FIG. 11 is an explanatory diagram showing a schematic configuration of an SPR measurement device which uses a flow cell according to a fourth embodiment of the present invention.
Figure 12:
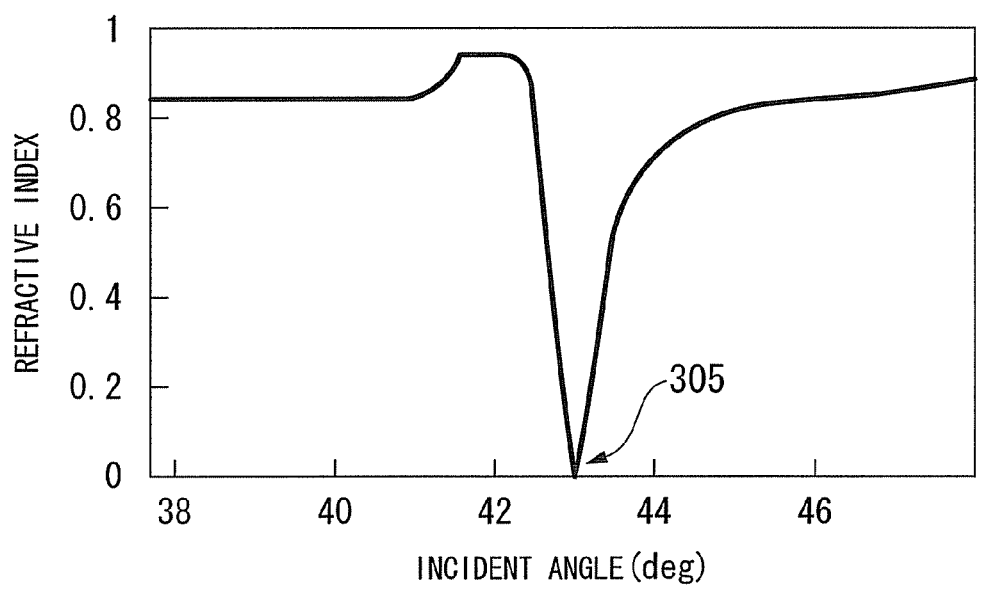
FIG. 12 is a characteristic diagram for describing a relationship between the reflectance and reflection angle of a detecting section measured with the SPR measurement device.
Figure 13:
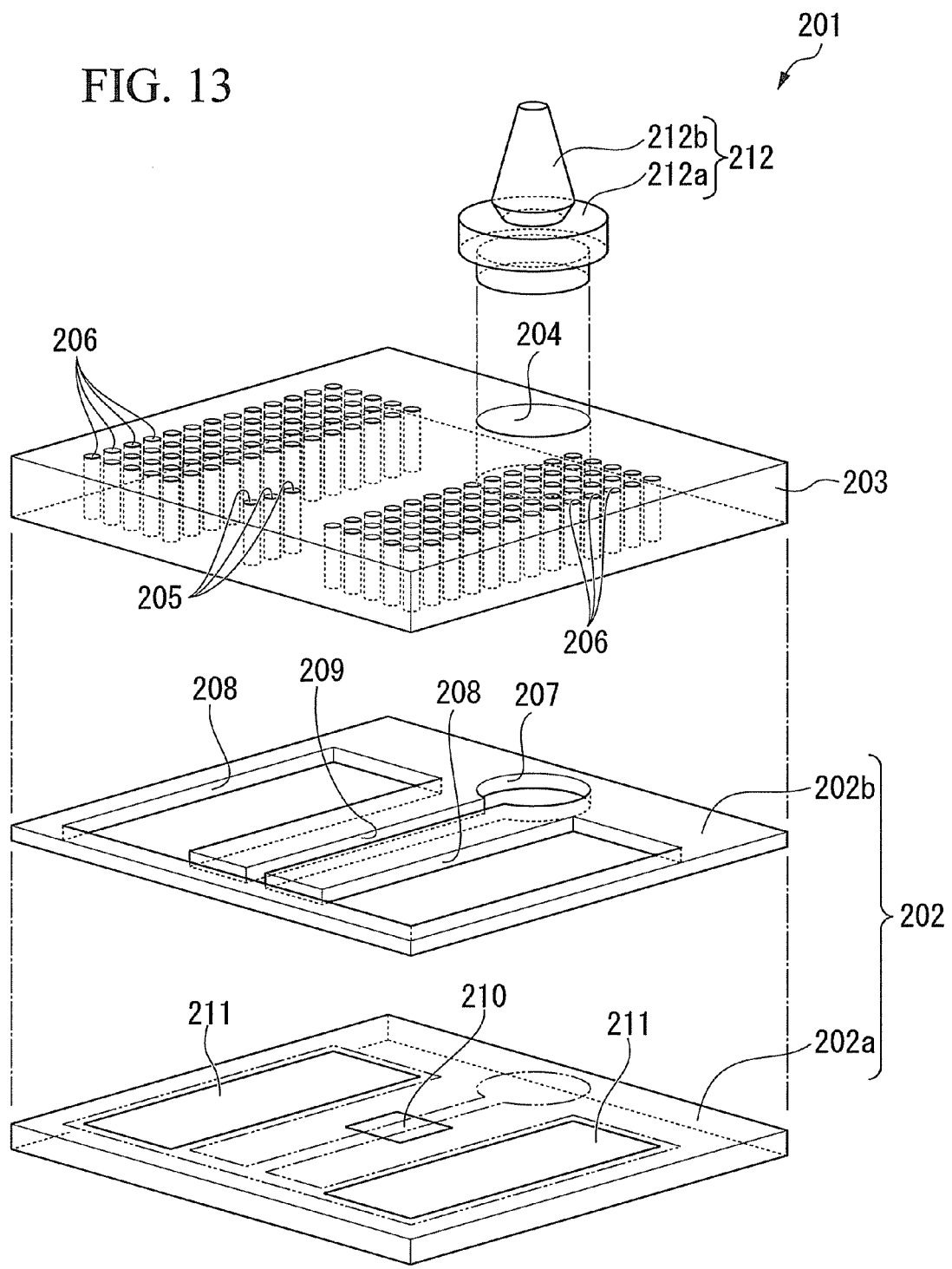
FIG. 13 is an exploded perspective view showing a schematic configuration of the flow cell according to the fourth embodiment of the present invention.
Figure 14:
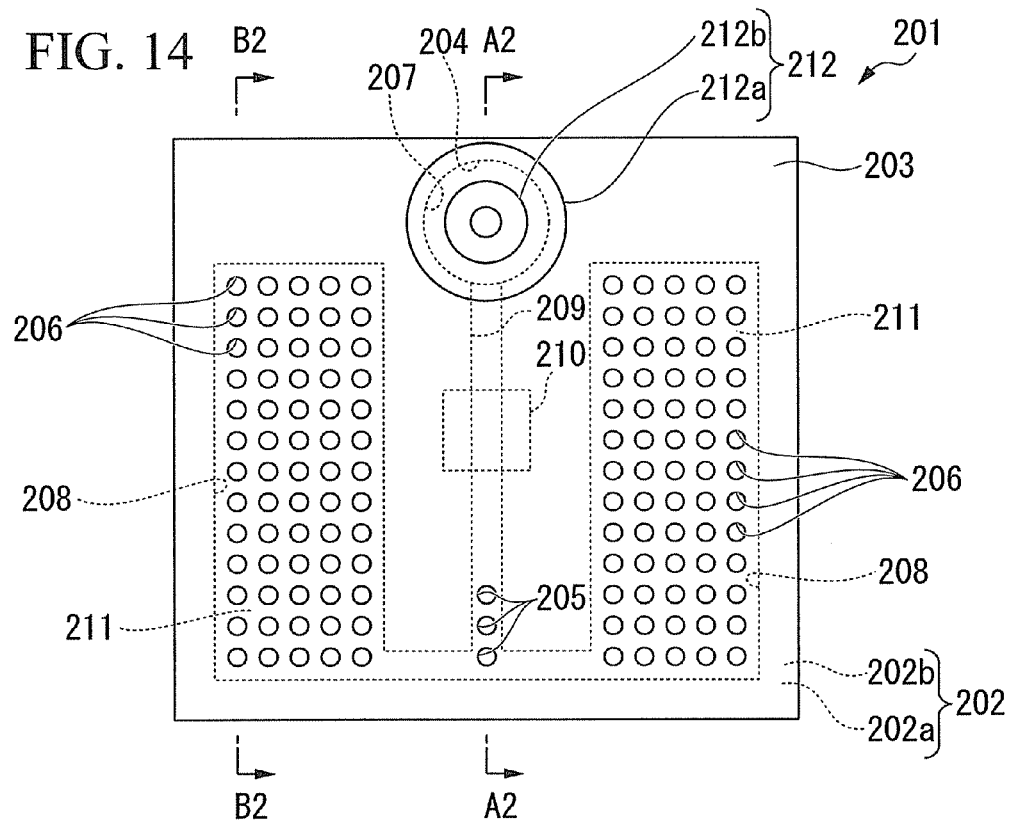
FIG. 14 is a plan view showing the schematic configuration of the flow cell according to the fourth embodiment of the present invention.
Figure 15:
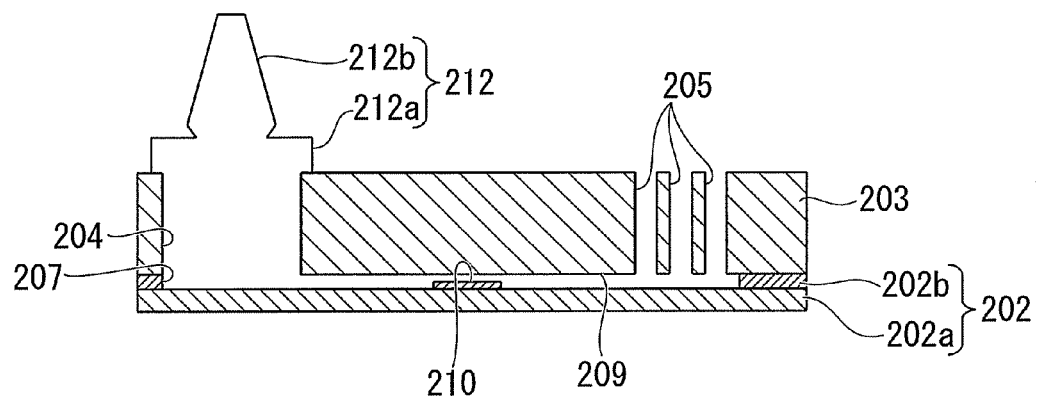
FIG. 15 is a sectional side view taken along the line A2-A2 in FIG. 14.
Figure 16:
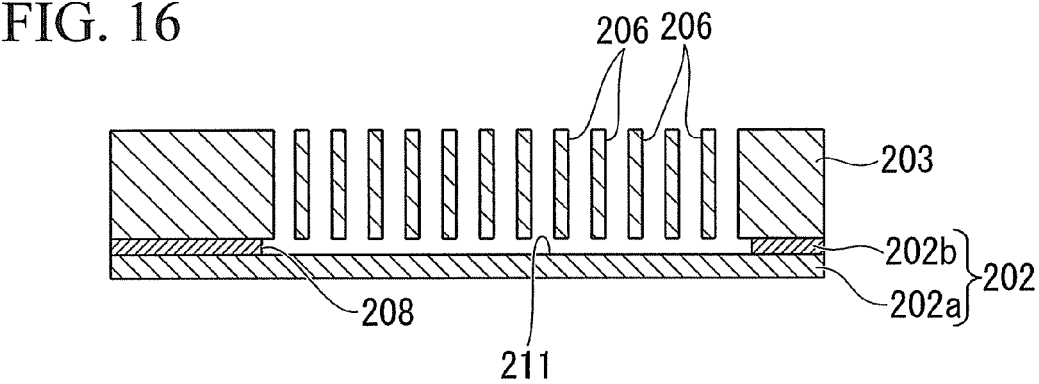
FIG. 16 is a sectional side view taken along the line B2-B2 in FIG. 14.
Figure 17:
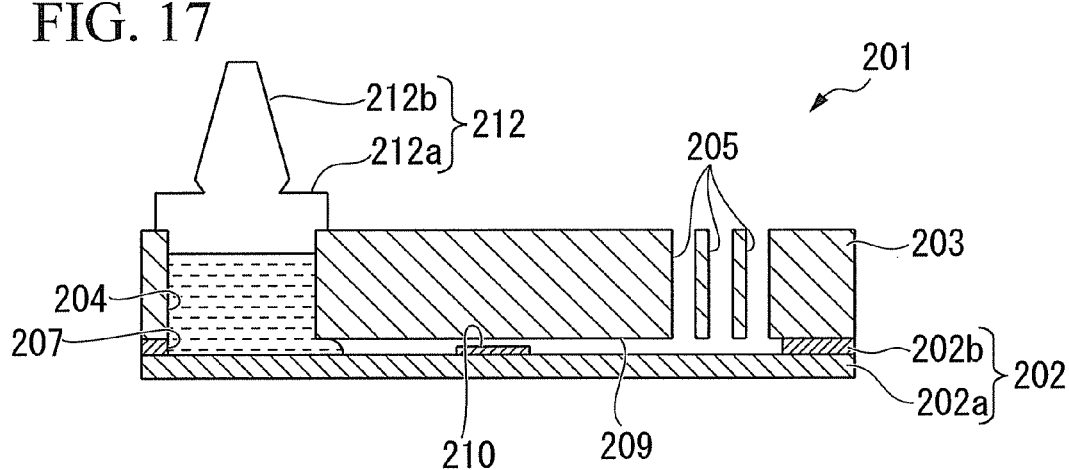
FIG. 17 is a sectional side view for describing an equilibrium state of the flow cell according to the fourth embodiment of the present invention before a reference solution is delivered to a detecting section.
Figure 18:
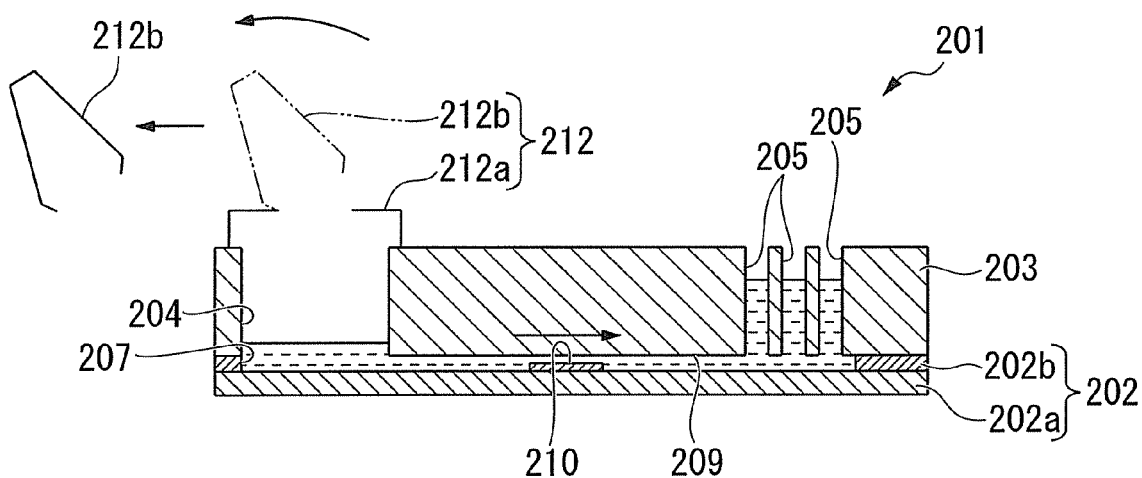
FIG. 18 is a sectional side view for describing an equilibrium state of the flow cell according to the fourth embodiment of the present invention after the reference solution is delivered to the detecting section.

FIG. 11 is an explanatory diagram showing a schematic configuration of an SPR measurement device which uses a flow cell according to a fourth embodiment of the present invention. FIG. 12 is a characteristic diagram for describing a relationship between the reflectance and reflection angle of a detecting section measured with the SPR measurement device. FIG. 13 is an exploded perspective view showing a schematic configuration of a flow cell according to the fourth embodiment of the present invention. FIG. 14 is a plan view showing the schematic configuration of the flow cell according to the fourth embodiment of the present invention. FIG. 15 is a sectional side view taken along the line A2-A2 in FIG. 14. FIG. 16 is a sectional side view taken along the line B2-B2 in FIG. 14. FIG. 17 is a sectional side view for describing an equilibrium state of the flow cell according to the fourth embodiment of the present invention before a reference solution is delivered to the detecting section. FIG. 18 is a sectional side view for describing an equilibrium state of the flow cell according to the fourth embodiment of the present invention after the reference solution is delivered to the detecting section.

A flow cell 201 of the present embodiment is installed on an SPR measurement device 300, which uses a so-called surface plasmon resonance (SPR) phenomenon, which is resonance between evanescent waves and surface plasmon waves on the surface of a metallic thin film, with which a detection target test specimen comes in contact, and it is used for performing measurements.

As shown in FIG. 11, this SPR measurement device 300 is such that light emitted from a light source 301 is polarized by a polarizer (not shown in the diagram) to provide P-polarized light (hereunder, referred to as "incident light"). Next, the SPR measurement device 300 causes the strip-shaped incident light concentrated by a condensing lens 302 to irradiate on the curved surface side of a half-columnar prism 303. Then, the SPR measurement device 300 performs irradiation on a metallic thin film described later of the flow cell 201 which is adhered on a measurement surface 303a on the planar surface side of this prism 303. Moreover, the SPR measurement device 300 detects the reflected light with a light receiving section 304 including a CCD image sensor.

When the intensity (light intensity) of the reflected light detected by the light receiving section 304 is detected, then as shown in FIG. 12, the reflection intensity decreases at an angle (resonance angle), at which the above resonance occurs. Therefore a valley 305 where the reflectance is low is observed. The resonance angle is dependent on the optical characteristic (refraction factor) of a sample solution which comes in contact with the metallic thin film. Therefore, by fixing an antibody on the metallic thin film and measuring the refractive index fluctuation caused by the bond between this antibody and an antigen, it is possible to perform a quantitative measurement of a specific substance.

As shown in FIG. 13 to FIG. 16, the flow cell 201 installed on the SPR measurement device 300 has a substantially rectangular solid outer shape or a substantially rectangular plate outer shape, and has a laminated structure. That is to say, in a state where the flow cell 201 is mounted on the SPR measurement device 300, there are provided a substantially rectangular plate-shaped lower substrate 202 arranged on the lower side, and an upper substrate 203 which is laminated on the upper side of the lower substrate 202 and the outer shape of which in plan view is formed in a shape substantially the same as that of the lower substrate 202. Moreover, for example, the plate thickness of the lower substrate 202 is approximately 1 mm, and the plate thickness of the upper substrate 203 is approximately 3 mm.

The upper substrate 203, on one end side of the substantially center (on the upper-right side in FIG. 13, or on the top side in FIG. 14) in the widthwise direction in a plan view thereof (in the upper-left to lower-right direction in FIG. 13, or in the left-right direction in FIG. 14), is provided with a columnar hole-shaped solution supply hole (inlet section) 204 for supplying respective solutions of a sample solution and a reference solution to be measured. The reference solution has properties approximate to those of the sample solution, and it is a solution which does not contain the test specimen of the sample solution to be measured. The solution supply hole 204 passes through the upper substrate 203 in the plate thickness direction thereof.

Moreover, in the upper substrate 203 there are provided a plurality of columnar hole-shaped first through holes (first transfer section) 205 and second through holes (second transfer section) 206, and they pass through the upper substrate 203 in the plate thickness direction thereof. A plurality of the second through holes 206 are arranged in a substantially rectangular shape in a plan view respectively on one side (on the left side in FIG. 14) and on the other side (on the right side in FIG. 14) in the widthwise direction. These second through holes 206 are of an aggregate of capillaries which draw in a sample solution supplied to the solution supply hole 204. These second through holes 206 are set to have an inner diameter within a range where the respective second through holes 206 exert a capillary action on the sample solution and draw in the sample solution when wet. These second through holes 206 have an upper end which opens to the outside air, and a lower end which communicates with a drawing flow channel 208 described later.

Moreover, on the other end side (on the lower side in FIG. 14) of the substantially widthwise center, there are arranged a plurality of the first through holes 205 in a direction orthogonal to the widthwise direction. These first through holes 205 are of an aggregate of capillaries which draw in a reference solution supplied to the solution supply hole 204. These first through holes 205 are set to have an inner diameter within a range where the respective first through holes 205 exert a capillary action on the reference solution and draw in the reference solution when wet. These first through holes 205 have an upper end which opens to the outside air, and a lower end which communicates with a flow channel 209 described later.

Furthermore, the lower substrate 202 is of a two-layer configuration, the lower side layer thereof is formed with a base substrate 202a made of a material, such as glass and acrylic polymer, which transmits light, and the upper side layer thereof is formed with a spacer section 202b made of a polymer film or the like.

The spacer section 202b has an opening portion formed therein so as to pass therethrough in the thickness direction. In this opening portion, in a position corresponding to the solution supply hole 204 of the upper substrate 203, there is formed a circular hole 207 having an inner diameter substantially the same as that of the solution supply hole 204. Moreover, in the spacer section 202b, there are provided the respective drawing flow channels 208 formed in a substantially rectangular hole shape so as to correspond to the outer shape of the plurality of the second through holes 206 arranged in a substantially rectangular shape in a plan view respectively on the one side and the other side in the widthwise direction of the upper substrate 203. The drawing flow channels 208 are set to an approximate height which does not form a clearance between the solution and the second through holes 206 thereabove when the sample solution is supplied, and the height thereof in the plate thickness direction is approximately 10 to 100 µm for example.

Moreover, in the substantially widthwise center of the spacer section 202b there is formed a flow channel 209 which extends in a direction orthogonal to the widthwise direction. The flow channel 209 has an end section on one end side thereof communicated with the circular hole 207, and an end section on the other end side thereof branches to the one side and the other side in the widthwise direction so as to communicate with the respective drawing flow channels 208. Furthermore, above the vicinity of the end section on the other end side of the flow channel 209 there are arranged the first through holes 205 of the upper substrate 203.

Furthermore, the flow channel 209 is of a substantially sectional rectangular shape, and for example, the widthwise sectional dimension orthogonal to the extending direction thereof is approximately 1 mm, and the dimension in the plate thickness direction (height) is approximately 10 to 100 µm, and these are set within a range where capillary action is exerted on the respective solutions.

Moreover, in this manner, the solution supply hole 204 and the first through holes 205 communicate with each other through the circular hole 207 and the flow channel 209. Furthermore, the first through holes 205 and the second through holes 206 communicate with each other through the flow channel 209 and the drawing flow channels 208.

Moreover, in the substantially widthwise center of the upper surface of the lower substrate 202a there is formed a rectangular metallic thin film (detecting section) 210. The metallic thin film 210 is, for example, made of Au (gold), and is arranged so as to be able to face and come in contact with the respective solutions flowing through the flow channel 209 of the spacer section 202b. Moreover, on the upper surface of the metallic thin film 210 there are arranged a plurality of antibodies (not shown in the diagram) along the flow channel 209. Although in the present embodiment, the metallic thin film 210 is arranged so as to correspond to a region in the substantially center on the upper surface of the base substrate 202a, which is used for measurement, the metallic thin film 210 may be formed broader and larger, exceeding the above region range.

Moreover, in a portion which corresponds to each of the drawing flow channels 208 of the spacer section 202b on the one side and on the other side in the width direction of the base substrate 202a, there is each formed a substantially rectangular surface active region 211. The surface active region 211 has undergone surface treatments, and it is set so that the wettability thereof with respect to the sample solution differs from that of the region other than the surface active region 211. That is to say, various types of surface treatments for the surface active region 211 are set to thereby vary and control the drawing state and flow rate of the sample solution.

Moreover, on the upper surface of the upper substrate 203 there is arranged an ampule (reserve section) 212 which is fitted on the solution supply hole 204. The ampule 212 is a liquid-sealed member in a closed container shape capable of accumulating a reference solution therein, and it includes a substantially multistage columnar main body section 212a and a substantially truncated cone-shaped protruding section 212b which communicates with the upper surface side of the main body section 212a. Furthermore, the lower end portion of the main body section 212a is formed so that the outer diameter thereof is slightly smaller and is substantially equal to the inner diameter of the solution supply hole 204, and it opens downward. Moreover, the base end portion of the protruding section 212b connected to the main body section 212a is formed with a slightly smaller outer diameter. By tilting the tip end portion of the protruding section 212b, this base end portion is separated so as to be away from the upper surface of the main body section 212a, and thereby the main body section 212a can be unsealed.

When manufacturing the flow cell 201, as shown in FIG. 17, a predetermined amount described later of the reference solution is preliminarily accumulated inside the main body section 212a of the ampule 212 and in the solution supply hole 204. The lower end of the accumulated reference solution remains on one end side of the flow channel 209. Liquid delivery is not made to the metallic thin film 210 of the flow channel 209 and the state shown in FIG. 17 is maintained until the protruding section 212b of the ampule 212 is separated from the main body section 212a and this main body section 212a is unsealed.

Next, there is described a procedure of measuring a sample solution with the SPR measurement device 300, using the flow cell 201 configured in this manner.

First, the flow cell 201 is mounted, via matching oil or the like, on the measurement surface 303a of the prism 303 of the SPR measurement device 300. In a state where the flow cell 201 is mounted in this way, incident light from the light source 301 is irradiated on the metallic thin film 210 of the flow cell 201, and the reflected light which is reflected is received by the light receiving section 304, creating a state where variations in refractive index can be measured.

Next, as shown in FIG. 18, the protruding section 212b of the ampule 212 of the solution supply hole 204 of the mounted flow cell 201 is tilted and separated from the main body section 212a, to thereby unseal the main body section 212a. When the main body section 212a is unsealed in this manner, the solution supply hole 204 delivers the accumulated reference solution to the flow channel 209 so as to draw in the outside air. That is to say, the reference solution is guided to the flow channel 209 as the flow channel 209 communicating with the solution supply hole 204 exerts the capillary action. Then, it is drawn in due to the capillary action caused by the first through holes 205, which are arranged in the vicinity of the end section on the other end side of the flow channel 209, getting wetted with the reference solution, and it is continuously delivered to the metallic thin film 210. In this state, a measurement of the reference solution is performed.

Then when the force of drawing the reference solution comes to an equilibrium as shown in FIG. 18, delivery of the reference solution stops. In the state where the liquid delivery is stopped, the reference solution remains slightly on the bottom section of the solution supply hole 204, and it does not reach the upper end opening of the through holes 205. That is to say, the amount of reference solution to be preliminarily accumulated in the ampule 212 is set to an approximate amount, with which the reference solution remains slightly in the solution supply hole 204 in the equilibrium state after the liquid delivery as shown in FIG. 18.

Next, a sample solution is supplied to the solution supply hole 204 of the flow cell 201. When the sample solution is supplied, the reference solution which has already been delivered to the flow channel 209 is drawn in as the first through holes 205 exert the capillary action again, and the sample solution is guided to the flow channel 209. When these first through holes 205 are filled with the solution, these first through holes 205 no longer exert the capillary action. Then, the second through holes 206 communicating with the first through holes 205 draw in and guide the sample solution to the flow channel 209 due to the capillary action caused by the state of being wetted with the remaining reference solution and the following sample solution, and thereby it is continuously delivered to the metallic thin film 210. In this state, a measurement of the sample solution is performed.

As described above, according to the flow cell 201 of the fourth embodiment, the ampule 212 is provided so as to communicate with the solution supply hole 204 so that the reference solution is accumulated in the solution supply hole 204. By unsealing the upper surface of the main body section 212a of this ampule 212, the outside air is drawn in from the unsealed portion, and the accumulated reference solution is flowed to the metallic thin film 210 of the flow channel 209. Therefore, when performing a measurement, the operator does not need to supply the reference solution from the outside every time, and is able to deliver the accumulated reference solution to the metallic thin film 210 with just a simple operation of unsealing the ampule 212.

Consequently, there is no need for a complex device configuration in which the reference solution and the sample solution are respectively supplied to the flow cell 201, using a plurality of syringe pumps, a liquid switch, a tube, and the like for example, as practiced heretofore, so that the cost of equipment can be reduced. Moreover, there is no need for performing complex operations such as replacing, cleaning, and drying these syringe pumps, the liquid switch, the tube and the like at each measurement so that workability is improved.

Furthermore, since the amount the reference solution to be delivered is set to a predetermined amount preliminarily accumulated in the solution supply hole 204, there is no need for performing a complex operation as practiced heretofore in which the operator adjusts the amount of reference solution to be supplied to the flow cell 201 at each measurement. Moreover, the amount of the reference solution to be accumulated in the solution supply hole 204 is set so that it partially remains in the solution supply hole 204 in an equilibrium state where the liquid delivery is stopped. Therefore when supplying the sample solution following the reference solution, the following problems encountered heretofore will not occur.

That is to say, heretofore the operator passively performed the operation with attention to the amount of decrease in the reference solution remaining in the solution supply hole 204, and supplied the sample solution to the solution supply hole 204 in a state where all of the reference solution has been transferred from the solution supply hole 204 and has become empty. Therefore, there was formed an air gap between the solutions flowing through the flow channel 209, so that a significant variation in measurement results referred to as a so-called injection shock occurred. Therefore, it was impossible to make a comparison in the trace amount of variation between the measurement result of the sample solution and the measurement result of the reference solution. In the present embodiment, this type of problem can be solved.

That is to say, since the operator who has delivered the reference solution is able to supply the next sample solution to the flow cell 201 and actively perform liquid delivery in accordance with the operation, a high level of proficiency is not required for the operator, and the operation can be performed simply, ensuring a sufficient level of measurement precision.

Moreover, even in those cases where a plurality of measurement devices are used and measurements are performed in parallel using a plurality of flow cells 201, the operator can simply perform liquid delivery in accordance with the operation. Therefore errors will not occur in the operation. Since the timing of liquid delivery can be adjusted in accordance with the operation, the reference solution can be flowed immediately before measuring the sample solution to thereby perform a measurement, and the metallic thin film 210 of the flow channel 209 will not be exposed to the reference solution for a prolonged period of time, thereby further increasing the level of measurement precision. That is to say, for example, the reference solution is preliminarily accumulated and stored in the flow channel 209 of the flow cell 201. In a case where the sample solution is supplied to the flow cell 201 to perform a measurement of the sample solution after having performed a measurement of the reference solution first with use of this flow cell 201, the metallic thin film 210 facing the flow channel 209 is exposed to the reference solution for a prolonged period of time. Therefore, it may be considered that the activity of the antibody is reduced and this may influence the measurement precision. However, in the present embodiment, since the reference solution is delivered to the metallic thin film 210 of the flow channel 209 immediately before the measurement, the level of measurement precision is sufficiently ensured.

Next, a fifth embodiment of the present invention is described, with reference to FIG. 19 to FIG. 22.

Figure 19:
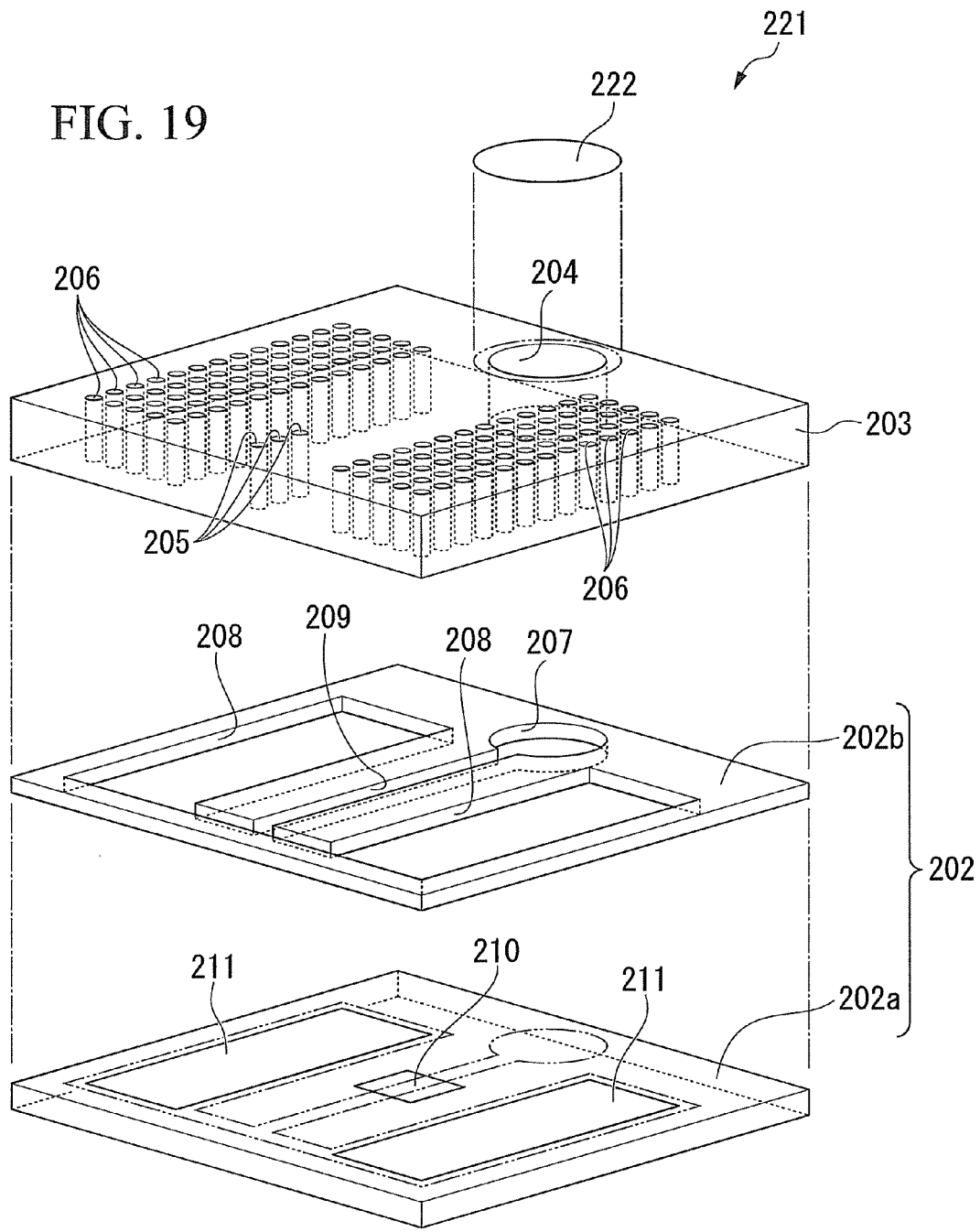
FIG. 19 is an exploded perspective view showing a schematic configuration of a flow cell according to a fifth embodiment of the present invention.
Figure 20:
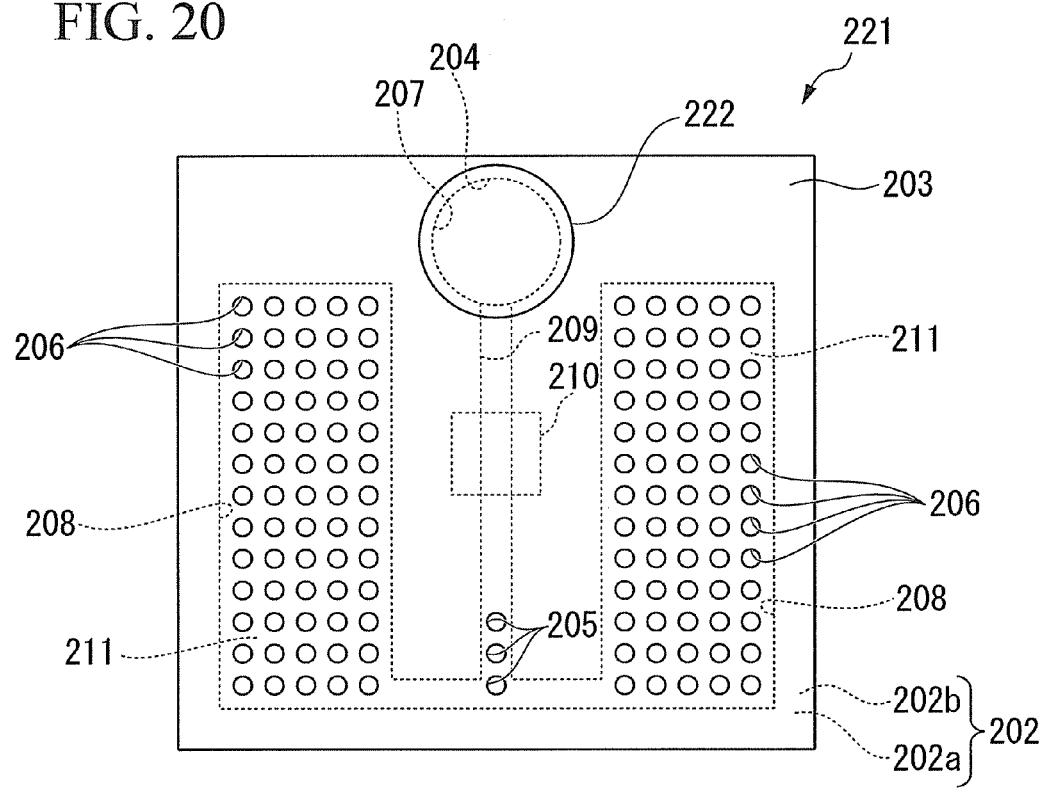
FIG. 20 is a plan view showing the schematic configuration of the flow cell according to the fifth embodiment of the present invention.
Figure 21:
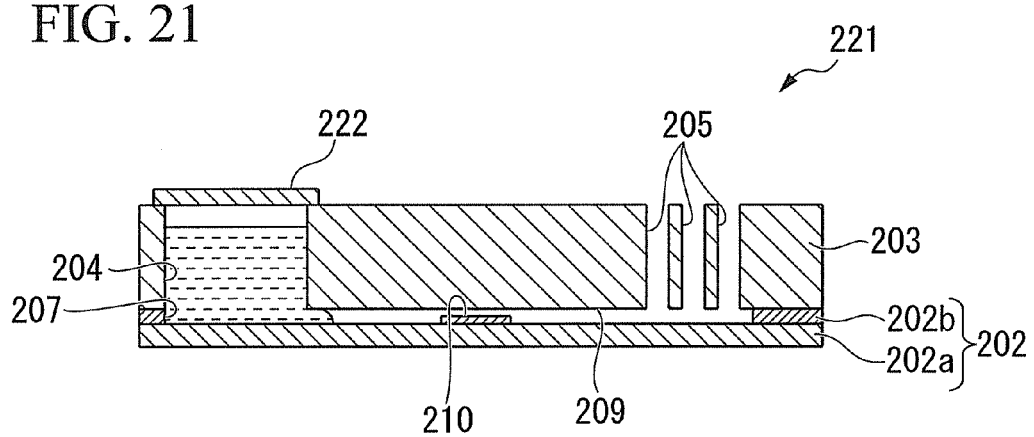
FIG. 21 is a sectional side view for describing an equilibrium state of the flow cell according to the fifth embodiment of the present invention before a reference solution is delivered to a detecting section.
Figure 22:
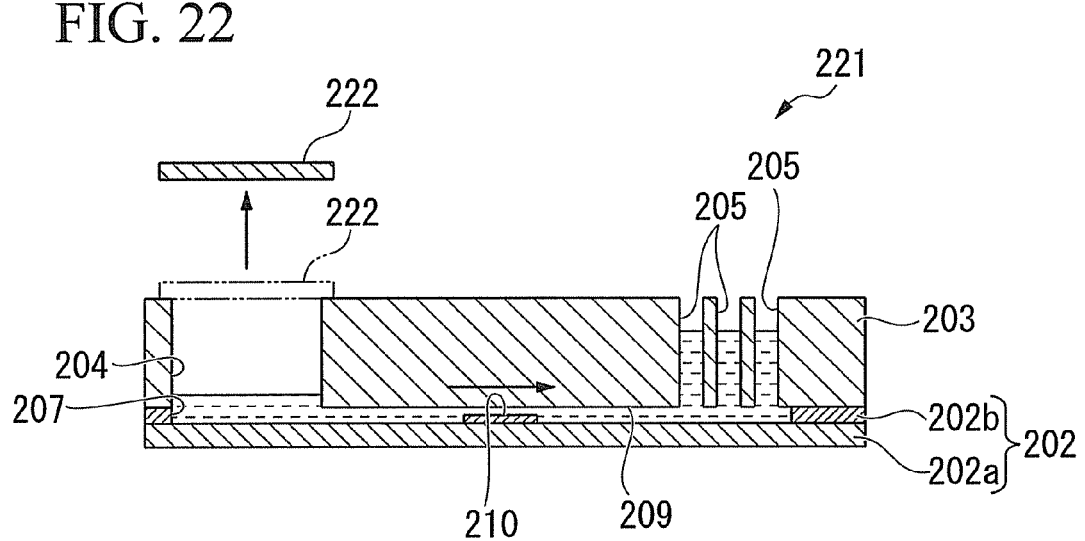
FIG. 22 is a sectional side view for describing an equilibrium state of the flow cell according to the fifth embodiment of the present invention after the reference solution is delivered to the detecting section.

FIG. 19 is an exploded perspective view showing a schematic configuration of a flow cell according to the fifth embodiment of the present invention. FIG. 20 is a plan view showing the schematic configuration of the flow cell according to the fifth embodiment of the present invention. FIG. 21 is a sectional side view for describing an equilibrium state of the flow cell according to the fifth embodiment of the present invention before a reference solution is delivered to the detecting section. FIG. 22 is a sectional side view for describing an equilibrium state of the flow cell according to the fifth embodiment of the present invention after the reference solution is delivered to the detecting section.

Members the same as those in the fourth embodiment described above are denoted by the same reference symbols, and descriptions thereof are omitted.

As shown in FIG. 19 and FIG. 20, on the upper surface of an upper substrate 203 of a flow cell 221 of the fifth embodiment, there is attached a sheet-shaped inlet section sealing member (reserve section) 222 formed with a substantially circular adhesive tape having a diameter greater than the inner diameter of a solution supply hole 204, so as to seal the opening of the solution supply hole 204. The inlet section sealing member 222 can be detached from the upper substrate 203 to thereby unseal the solution supply hole 204.

When manufacturing the flow cell 221, as shown in FIG. 21, the inlet section sealing member 222 is attached so as to seal the opening of the solution supply hole 204 in a state where only a predetermined amount of the reference solution is preliminarily accumulated inside the solution supply hole 204. Consequently, the accumulated reference solution remains on one end side of the flow channel 209, and the state shown in FIG. 21 is maintained. That is to say, the reference solution is not delivered to the metallic thin film 210 of the flow channel 209 until the inlet section sealing member 222 has been detached from the upper substrate 203 and the solution supply hole 204 has been unsealed.

Next, in order to measure a sample solution with the SPR measurement device 300, using the flow cell 221 configured in this manner, the following process is performed. First, incident light from a light source 301 is irradiated on the metallic thin film 210 of the flow cell 221 in the state where the flow cell 221 is mounted, via matching oil or the like, on the measurement surface 303a of a prism 303 of the SPR measurement device 300. Then, the reflected light which is reflected is received by a light receiving section 304, creating a state where variations in refractive index can be measured.

Next, as shown in FIG. 22, the inlet section sealing member 222 of the solution supply hole 204 of the mounted flow cell 221 is detached to thereby unseal the solution supply hole 204. When the solution supply hole 204 is unsealed in this manner, first through holes 205 draw up the reference solution. Then, the solution supply hole 204 delivers the accumulated reference solution to the metallic thin film 210 of the flow channel 209 so as to drawn in the outside air. In this state, a measurement of the reference solution is performed.

Then when the force of drawing the reference solution comes to an equilibrium as shown in FIG. 22, delivery of the reference solution stops. The setting is such that in the state where liquid delivery is stopped, the reference solution remains slightly on the bottom section of the solution supply hole 204.

Next, a sample solution is supplied to the solution supply hole 204 of the flow cell 221. The supplied sample solution is guided to the flow channel 209 and continuously delivered to the metallic thin film 210. In this state, a measurement of the sample solution is performed.

As described above, according to the flow cell 221 of the fifth embodiment, the opening of the solution supply hole 204 accumulating the reference solution is sealed by the inlet section sealing member 222. Then if the inlet section sealing member 222 is detached from the solution supply hole 204 to unseal it in accordance with the operation, the solution supply hole 204 delivers the accumulated reference solution to the metallic thin film 210 of the flow channel 209 so as to draw in the outside air from the unsealed portion. Therefore, liquid delivery can be performed easily with a simple configuration, and the cost of manufacturing can be reduced.

Next, a sixth embodiment of the present invention is described, with reference to FIG. 23 to FIG. 26.

Figure 23:
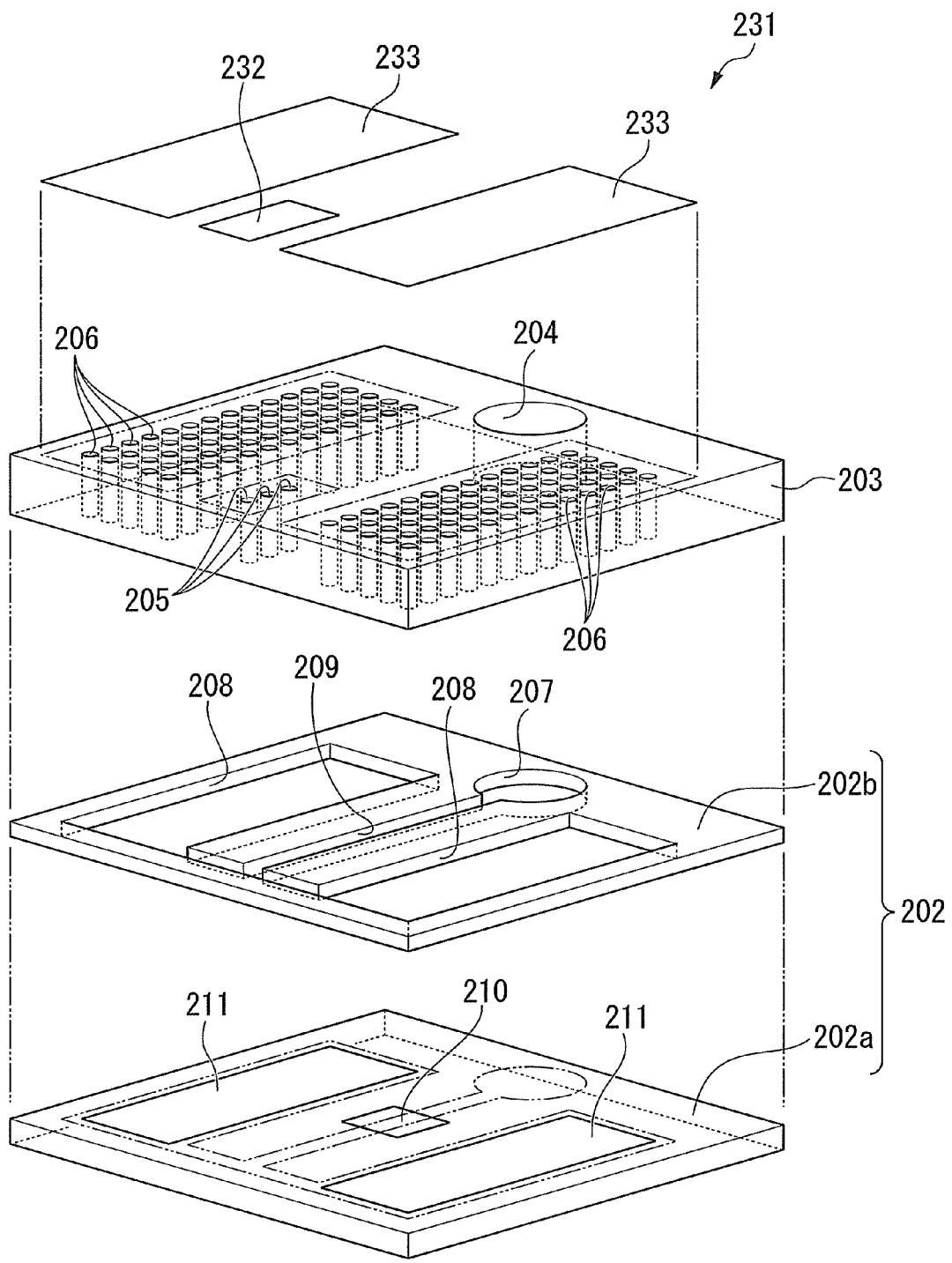
FIG. 23 is an exploded perspective view showing a schematic configuration of a flow cell according to a sixth embodiment of the present invention.
Figure 24:
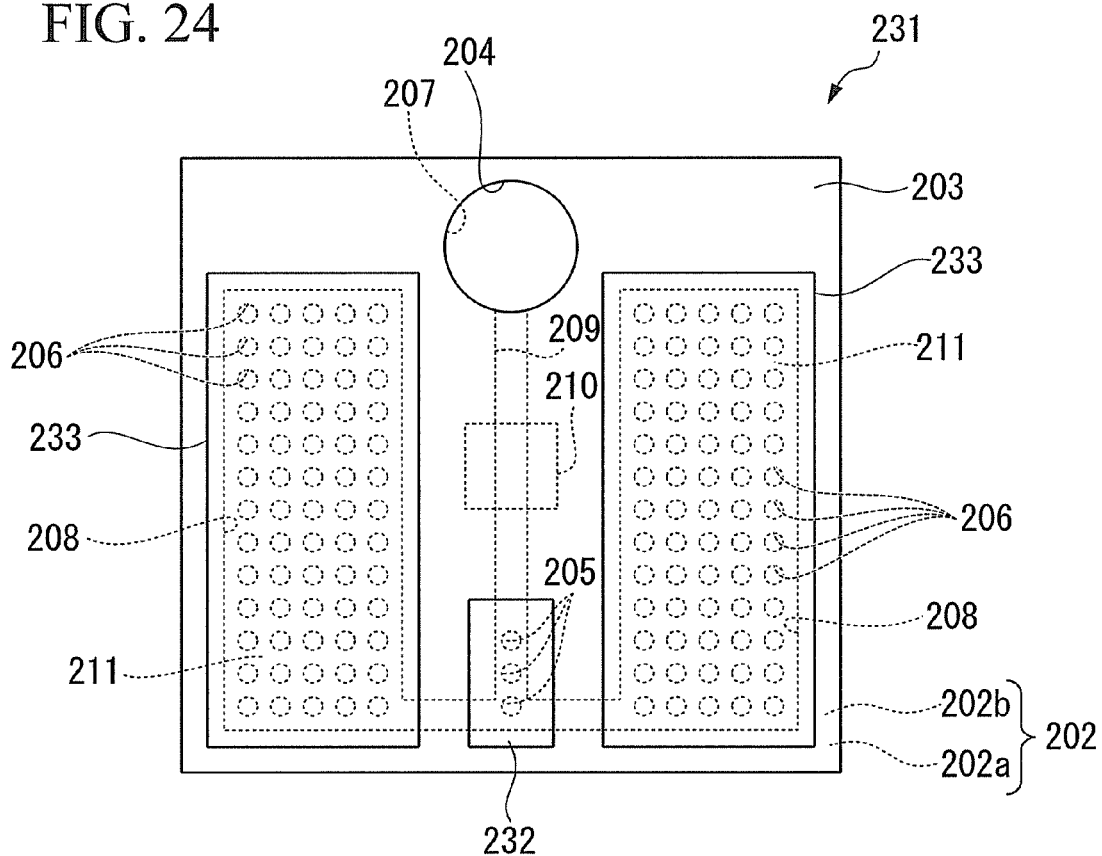
FIG. 24 is a plan view showing the schematic configuration of the flow cell according to the sixth embodiment of the present invention.
Figure 25:
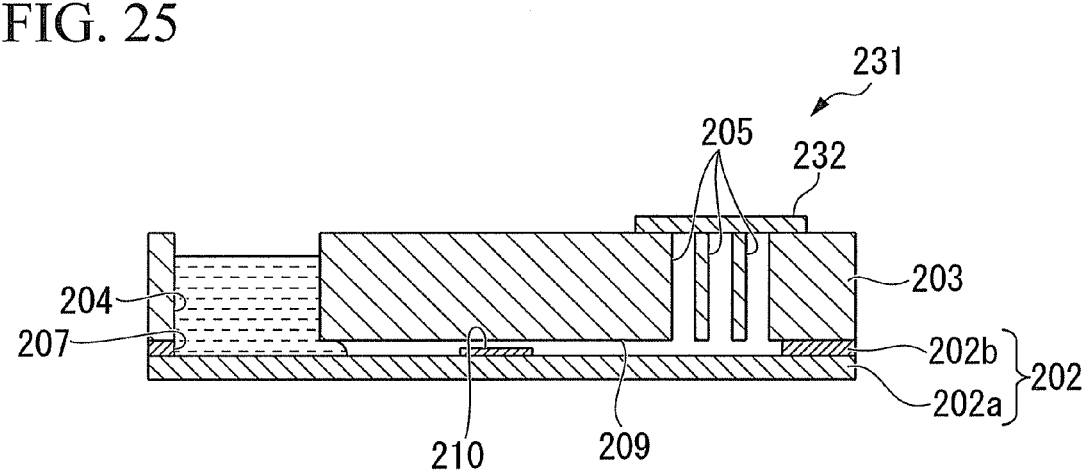
FIG. 25 is a sectional side view for describing an equilibrium state of the flow cell according to the sixth embodiment of the present invention before a reference solution is delivered to a detecting section.
Figure 26:
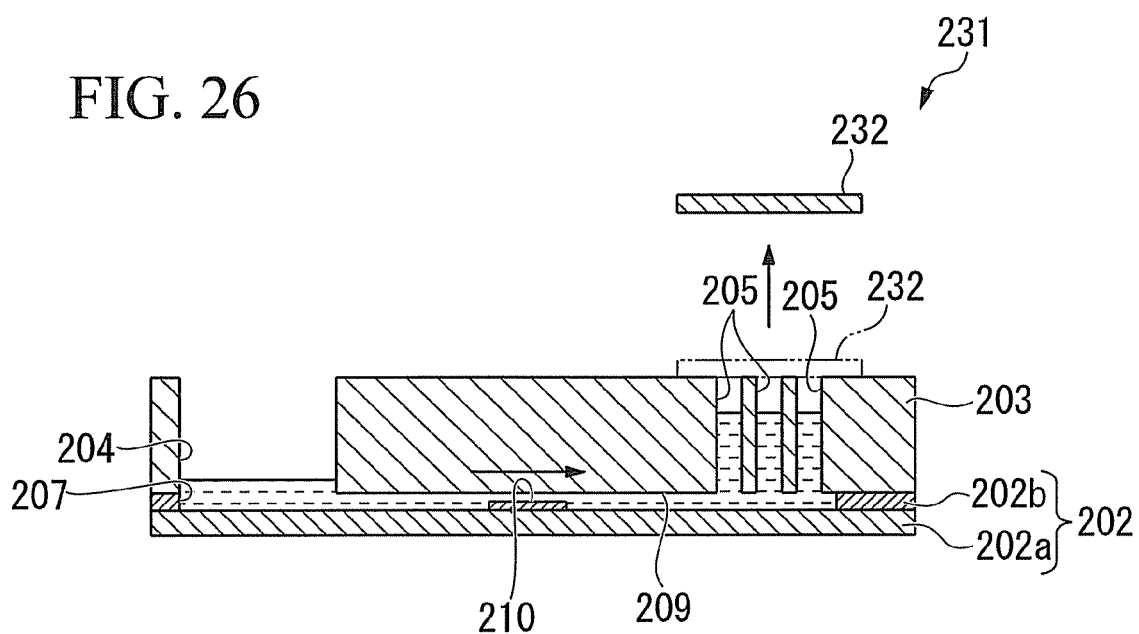
FIG. 26 is a sectional side view for describing an equilibrium state of the flow cell according to the sixth embodiment of the present invention after the reference solution is delivered to the detecting section.

FIG. 23 is an exploded perspective view showing a schematic configuration of a flow cell according to the sixth embodiment of the present invention. FIG. 24 is a plan view showing the schematic configuration of the flow cell according to the sixth embodiment of the present invention. FIG. 25 is a sectional side view for describing an equilibrium state of the flow cell according to the sixth embodiment of the present invention before a reference solution is delivered to the detecting section. FIG. 26 is a sectional side view for describing an equilibrium state of the flow cell according to the sixth embodiment of the present invention after the reference solution is delivered to the detecting section.

Members the same as those in the fourth and fifth embodiments described above are denoted by the same reference symbols, and descriptions thereof are omitted.

As shown in FIG. 23 and FIG. 24, on the upper surface of an upper substrate 203 of a flow cell 231 of the sixth embodiment, there is attached a first sealing member (reserve section) 232 formed with a substantially rectangular adhesive tape so as to seal the opening of first through holes 205. The first through holes 205 can be unsealed by detaching the first sealing member 232 from the upper substrate 203.

Moreover, on the upper surface of the upper substrate 203, there are respectively attached a pair of second sealing members (reserve sections) 233 each formed with a substantially rectangular adhesive tape so as to cover a portion which corresponds to the outer shape of the second through holes 206 arranged in a substantially rectangular shape on the widthwise one side (on the left side in FIG. 24), and a portion which corresponds to the outer shape of the second through holes 206 arranged in a substantially rectangular shape on the other side (on the right side in FIG. 24). Thereby, the openings of these second through holes 206 are sealed. The respective second through holes 206 can be unsealed by detaching these second sealing members 233 from the upper substrate 203.

When manufacturing the flow cell 231, as shown in FIG. 25, the first sealing member 232 is attached on the upper end opening of the first through holes 205 to thereby seal these first through holes 205. Furthermore, the respective second sealing members 233 are adhered on the openings of the second through holes 206 on the widthwise one side and on the opening of the second through holes 206 on the other side, to thereby seal these second through holes 206. In this state, a predetermined amount of a reference solution is accumulated inside a solution supply hole 204. Consequently, the reference solution accumulated in the solution supply hole 204 remains on one end side of the flow channel 209, and the state shown in FIG. 25 is maintained.

Next, a sample solution is measured with the SPR measurement device 300, using the flow cell 231 with this type of configuration. First, incident light from a light source 301 is irradiated on the metallic thin film 210 of the flow cell 231 in the state where the flow cell 231 is mounted, via matching oil or the like, on the measurement surface 303a of a prism 303 of the SPR measurement device 300. Then, the reflected light is received by a light receiving section 304, creating a state where variations in refractive index can be measured.

Next, as shown in FIG. 26, the first sealing member 232 of the first through holes 205 of the mounted flow cell 231 is detached to thereby unseal the first through holes 205. When the first through holes 205 are unsealed, the first through holes 205 draw up the reference solution. Then, the solution supply hole 204 delivers the accumulated reference solution to the metallic thin film 210 of the flow channel 209 so as to drawn in the outside air. In this state, a measurement of the reference solution is performed.

Then when the force of drawing the reference solution comes to an equilibrium as shown in FIG. 26, delivery of the reference solution stops. The setting is such that in the state where liquid delivery is stopped, the reference solution remains slightly on the bottom section of the solution supply hole 204.

Next, a sample solution is supplied to the solution supply hole 204 of the flow cell 231. The supplied sample solution remains on one end side of the flow channel 209 in a state of being accumulated in the solution supply hole 204, and it is not delivered, thereby creating an equilibrium state. Next, when the second sealing members 233 are detached and the second through holes 206 are thereby unsealed, the sample solution accumulated in the solution supply hole 204 is delivered continuously to the metallic thin film 210 with a guidance of the flow channel 209. In this state, a measurement of the sample solution is performed.

As described above, according to the flow cell 221 of the sixth embodiment, the first sealing member 232 is attached on the opening of the first through holes 205 to seal them in the state where the reference solution is accumulated in the solution supply hole 204. Then if the first sealing member 232 is detached from the first through holes 205 to thereby unseal the first through holes 205 in accordance with the operation, the solution supply hole 204 delivers the accumulated reference solution to the metallic thin film 210 of the flow channel 209 so as to draw in the outside air. Therefore, liquid delivery can be performed easily with a simple configuration, and the cost of manufacturing can be reduced.

Moreover, the openings of the second through holes 206 are sealed by the second sealing members 233. Therefore, the sample solution supplied to the solution supply hole 204 is not delivered to the flow channel 209 and is accumulated in the solution supply hole 204 until the second sealing members 233 have been detached from the second through holes 206 to unseal them. That is to say, by detaching the second sealing members 233 from the second through holes 206 and unsealing them, the solution supply hole 204 delivers the accumulated sample solution to the metallic thin film 210 of the flow channel 209 so as to draw in the outside air. Therefore, the timing of sample solution delivery can be actively controlled with a simple configuration, and workability is improved.

The present invention is not limited to the aforementioned embodiments, and various types of modifications may be made thereto without departing from the scope of the invention.

For example, the fourth embodiment describes use of the ampule 212 as the liquid-sealed member of the reserve section; however, there may be provided a configuration in which the reference solution can be accumulated in the solution supply hole 204 and the solution supply hole 204 can be unsealed. Furthermore, it is not limited to this, and there may be used other types of containers such as a micro-capsule or a closed container.

Moreover, the second sealing members 233 described in the sixth embodiment may be used for the fourth and fifth embodiments, thereby providing a configuration in which the second through holes 206 can be unsealed. In this case, also in the fourth and fifth embodiments, the operator can actively control the timing of delivering the sample solution in accordance with the operation. Therefore measurement precision is increased and workability is improved.

Furthermore, in the fourth to sixth embodiments, the measurement of the reference solution and the measurement of the sample solution are described as being performed once respectively. However, it is not limited to this, and having measured the sample solution, the second reference solution may be supplied to the solution supply hole 204 to perform a measurement, and the measurement result of the sample solution may be analyzed using the first and second measurement results of the reference solution. Moreover, the reference solution may be measured three times or more, and the measurement result of the sample solution may be analyzed using these measurement results of the reference solution.

Furthermore, in the present embodiment, the first through holes 205 are described as the first transfer sections, and the second through holes 206 are described as the second transfer sections; however, they are not limited to these. For example, the first transfer section and the second transfer section may be configured with a flow channel, a cavity or the like which exerts a capillary action to thereby draw in the respective solutions.

Moreover, the shape, number, and arrangement of the first through holes 205 and the second through holes 206 are not limited to the present embodiment, and they may be set in various ways according to requirements and/or purposes.

Moreover, in the present embodiment, the flow cell is described as being used with the SPR measurement device 300; however, it may be applied to other devices on which a sample solution is flowed and measured. That is to say, an application may be made in areas where sample solutions are handled such as micro TAS, Lab on a chip, micro combinatorial chemistry, chemical IC, chemical sensors, biosensors, microanalysis, electrochemical analysis, chromatography, QCM measurement, and ATR measurement.

Next, a seventh embodiment of the present invention is described. Descriptions of parts in the seventh embodiments similar to those in the first embodiment are omitted.

A flow cell according to the seventh embodiment is such that there is provided a flow channel 9a instead of the flow channel 9 in the first embodiment. As with the flow channel 9 of the first embodiment (FIG. 4), the flow channel 9a of the seventh embodiment is linearly formed from a region where the circular hole 7 is provided to a region where the through holes 5 are provided.

Figure 27:
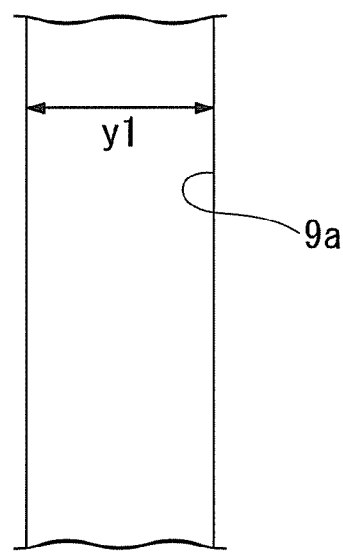
FIG. 27 is a plan view of a region where a metallic thin film 10 of a flow channel 9a according to a seventh embodiment of the present invention is not provided.

FIG. 27 is a plan view of a region (corresponding to the region Z1 in FIG. 4) where the metallic thin film 10 of the flow channel 9a according to the seventh embodiment of the present invention is not provided. The width of the flow channel 9a shown in FIG. 27 is y1.

Figure 28:
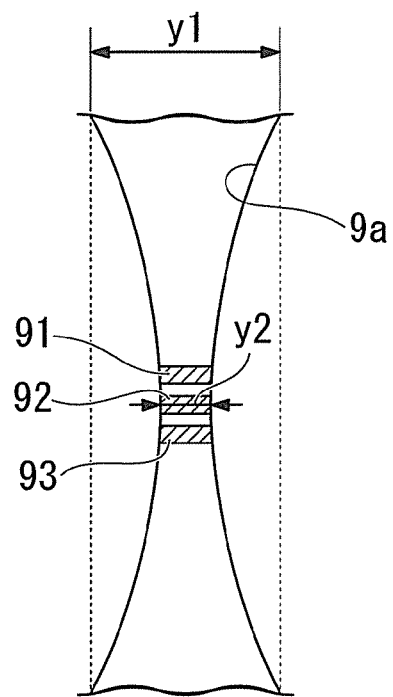
FIG. 28 is a plan view of a region where the metallic thin film 10 of the flow channel 9a according to the seventh embodiment of the present invention is provided.

FIG. 28 is a plan view of a region (corresponding to the region Z2 in FIG. 4) where the metallic thin film 10 of the flow channel 9a according to the seventh embodiment of the present invention is provided. The width of a flow channel 9b is y1 at both ends thereof, and the width in the center is y2. Moreover, y2 is smaller than y1. That is to say, the width of the flow channel 9a becomes narrower as it gets closer to the center from both ends.

In the vicinity of the center of the flow channel 9a of FIG. 28, there are provided antibodies 91, 92, and 93 arranged in an array. A liquid flowing within the flow channel 9a passes over the antibodies 91, 92, and 93.

Figure 29:
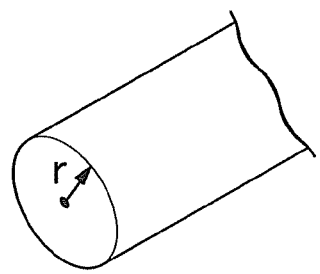
FIG. 29 is a diagram for describing a capillary force in a circular tube.

The capillary force F1 in the round tube shown in FIG. 29 is expressed by the following formula (1). The sectional surface of this round tube is a circle with radius r. Moreover, surface tension is γ and contact angle is θ.

$$F1 = -2\gamma \cos \theta / r \quad (1)$$

That is, the capillary force F1 which acts on the round tube in FIG. 29 is inversely proportional to the radius r of the sectional surface of the round tube.

Figure 30:
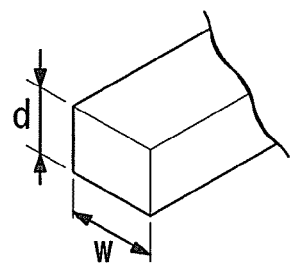
FIG. 30 is a diagram for describing a capillary force in a rectangular tube.

Moreover, the capillary force F2 in the rectangular tube shown in FIG. 30 is expressed by the following formula (2). The width of this rectangular tube is w and the height is d. Furthermore, the contact angle on the upper surface is $\theta_t$, the contact angle on the lower surface is $\theta_b$, the contact angle on the left surface is $\theta_1$, and the contact angle on the right surface is $\theta_r$.

$$F2 = -\gamma(\cos \theta_t / d + \cos \theta_b / d + \cos \theta_1 / w + \cos \theta_r / w) \quad (2)$$

That is, the capillary force F2 which acts on the rectangular tube shown in FIG. 30 is inversely proportional to the width w and height d of the sectional surface of the rectangular tube.

That is, in the seventh embodiment, the capillary force acts to a greater degree in the center than at both ends of the flow channel 9a on a liquid passing through the flow channel 9a in the region where the metallic thin film 10 is provided (FIG. 28). That is, the level of the capillary force becomes higher for a thinner tube, and therefore, a liquid flowing through a capillary tube becomes more stable when concentrated in a narrow portion. Therefore, a liquid such as the reference solution passing through the flow channel 9a in the region where the metallic thin film 10 is provided has a characteristic of being concentrated in the vicinity of the center.

As described in the first embodiment, the measurement of the reference solution and the like is performed in the flow channel in the region where the metallic thin film 10 is provided. In the seventh embodiment, the shape of the flow channel 9a in the region where the metallic thin film 10 is provided is of the configuration shown in FIG. 28. That is, the sectional area of the flow channel 9a in the region Z2 where the metallic thin film 10 (detecting section) is provided (refer to FIG. 28) is smaller than the sectional area of the flow channel 9a in the region Z1 where the metallic thin film 10 is not provided (FIG. 27). Furthermore, the width in the center of the flow channel 9a in the region Z2 where the metallic thin film 10 is provided is narrower than the width at both ends.

Therefore, after having flowed the reference solution, even in a process in which a period of time has elapsed and the reference solution is gradually evaporating, the reference solution remains in the region Z2 where the metallic thin film 10 is provided until the end. Therefore, it is possible to prevent the antibody from being exposed to the atmosphere, and to avoid reduction in the activity of the antibody due to dehydration.

In the seventh embodiment, there is described the case where the shape of the flow channel 9 of the first embodiment is changed; however, it is not limited to this. For example, the sectional shape of the flow channel of other embodiments may be in the configuration of the flow channel 9a according to the seventh embodiment.

Moreover, the shape of the flow channel in the region where the metallic thin film 10 is provided is not limited to the shape illustrated in FIG. 28. It is only necessary that the width at the center of the flow channel 9a where the metallic thin film 10 is provided be narrower than the width thereof at both ends. For example, there may be used a shape such that the width of the flow channel 9a in the region where the metallic thin film 10 is provided, becomes narrower linearly as it gets closer to the center from both ends.

In the first to sixth embodiments described above, it is possible to obtain an effect similar to that of the seventh embodiment without using the structure of the flow channel 9a of the seventh embodiment. The reason for this is described, with reference to FIG. 26 described for the sixth embodiment. That is to say, the sectional area of the flow channel 9 in the region where the metallic thin film 10 is provided is smaller than either one of the sectional area of the opening section of the solution supply hole 24 and the sectional area of the opening section of the first through hole 205. Therefore, the liquid is concentrated in the flow channel 9 in the region where the metallic thin film 10 is provided. Consequently, as with the seventh embodiment, it is possible to prevent the occurrence of injection shock and to prevent the antibody from dehydrating.

Next, an eighth embodiment of the present invention is described. Descriptions of parts in the eighth embodiment similar to those in the first embodiment are omitted.

In the first embodiment, there is described the case where a plurality of the opening sections 6 are sealed with a plurality of the sealing members 12 formed with an adhesive tape, and the user removes the sealing members 12 from the opening sections 6 as shown in FIG. 4 when the flow cell 1 is used.

Figure 31:
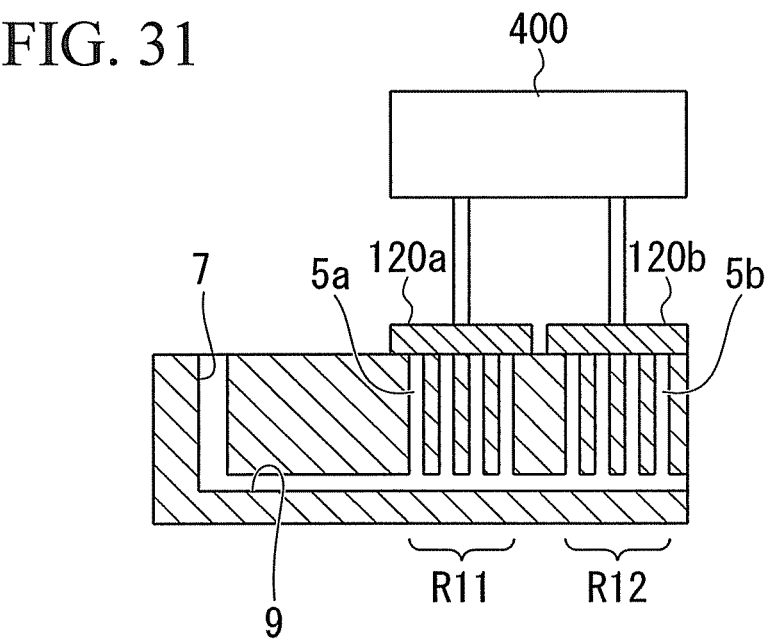
FIG. 31 is a schematic diagram showing a structure of a flow cell according to an eighth embodiment of the present invention.
Figure 32:
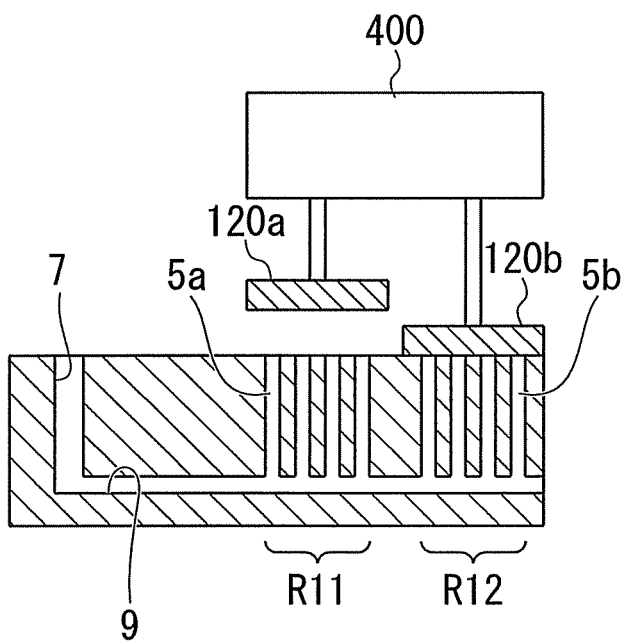
FIG. 32 is a schematic diagram showing the structure of the flow cell according to the eighth embodiment of the present invention.

FIG. 31 and FIG. 32 are schematic diagrams showing a structure of a flow cell according to the eighth embodiment of the present invention. In the eighth embodiment, there is used an external device 400. The external device 400 includes pads 120a and 120b (sealing member) capable of vertical movements.

The pad 120a seals the opening section of through holes 5a formed in a region R11 of the flow cell. Moreover, the pad 120b seals the opening section of through holes 5b formed in a region R12 of the flow cell different from the region R11. The pads 120a and 120b can be independently moved in the vertical direction in a direction parallel with the depth direction of the through holes 5a and 5b of the flow cell, based on control of the external device 400.

Before using the flow cell according to the eighth embodiment, as shown in FIG. 31, the opening sections of the through holes 5a and 5b formed in the regions R11 and R12 are both sealed by the pads 120a and 120b.

With an instruction from the user of the flow cell to open the opening sections of the through holes 5a formed in the region R11 given to a driving mechanism (not shown in the diagram), the pad 120a which has been sealing the through holes 5a is separated from the through holes 5a. As a result, the liquid supplied from the circular hole 7 flows through the flow channel 9 and the through holes 5a, and flows out from the opening sections of the through holes 5a to the outside of the flow cell.

Here, there has been described the case where the opening sections of the through holes 5a are changed from a sealed state to an open state by driving the pad 120a, however, it is not limited to this. For example, the opening sections of the through holes 5a may be changed from an open state to a sealed state by driving the pad 120a.

Here, there has been described the case where the sealed state and open state of the pad 120a is controlled based on an instruction from the user of the flow cell; however, it is not limited to this. For example, the sealed state and open state of the pad 120a may be switched at a predetermined time. Moreover, the sealed state and open state of the pad 120a may be switched if a predetermined condition is satisfied, for example, if the flow rate of a liquid flowing through the flow cell becomes below a predetermined rate.

INDUSTRIAL APPLICABILITY

The present invention may be applied to a flow cell and a liquid delivery method capable of adjusting the liquid delivery timing and liquid delivery amount of a sample solution in accordance with an operation.

REFERENCE SYMBOLS

1, 21, 41 Flow cell
4, 24 Solution supply hole (inlet section)
5 Through hole (transfer section)
6, 26 Opening section
9, 30 Flow channel
10, 31 Metallic thin film (detecting section)
12, 32, 52 Sealing member
25, 45 Chamber (transfer section)
27, 47 Columnar member (transfer section)
46 Concave section (opening section)
201, 221, 231 Flow cell
204 Solution supply hole (inlet section)
205 First through hole (first transfer section)
206 Second through hole (second transfer section)
209 Flow channel
210 Metallic thin film (detecting section)
212 Ampule (reserve section)
222 Inlet section sealing member (reserve section)
232 First sealing member (reserve section)
233 Second sealing member

The invention claimed is:

1. A flow cell comprising:
a flow channel through which a sample solution flows;
an inlet section which communicates with the flow channel and to which the sample solution is supplied;
a transfer section which includes a plurality of opening sections, each of the opening sections extending from a first end to a second end, the first end communicating with the flow channel and the second end opening to outside air, and the transfer section communicating with the flow channel, and drawing in and guiding the sample solution supplied into the inlet section to the flow channel;
a detecting section which faces the sample solution in the flow channel; and
a sealing member which unsealably seals at least either one of the opening section or the inlet section,
wherein the transfer section includes: a plurality of chambers, one end of which communicates with the flow channel and an other end of which is the opening section; and a plurality of columnar members arranged inside the chambers while having a clearance therebetween.

2. A flow cell comprising:
a flow channel through which a sample solution flows;
an inlet section which communicates with the flow channel and to which the sample solution is supplied;
a transfer section which includes a plurality of opening sections, each of the opening sections extending from a first end to a second end, the first end communicating with the flow channel and the second end opening to outside air, and the transfer section communicating with the flow channel, and drawing in and guiding the sample solution supplied into the inlet section to the flow channel;
a detecting section which faces the sample solution in the flow channel;
a sealing member which unsealably seals at least either one of the opening section or the inlet section; and
a reserve section which causes the inlet section to accumulate the reference solution having properties approximate to those of the sample solution and used for measurement comparison, and which is unsealable,
wherein the transfer section includes a first transfer section which communicates with an other end side of the flow channel, and draws in and guides the reference solution accumulated in the inlet section to the flow channel, and
the accumulated reference solution is delivered to the detecting section of the flow channel by unsealing the reserve section.

3. The flow cell according to claim 1,
wherein the sealing member is attached at least to either one of the opening section and the inlet section, and the sealing member is detachable.

4. The flow cell according to claim 1,
wherein the sealing member has a rod shape which blocks the opening section at a base end thereof, and a tip end thereof is tilted to open the opening section.

5. The flow cell according to claim 1,
wherein the transfer section includes a plurality of through holes.

6. The flow cell according to claim 2,
wherein there is provided a second transfer section which communicates with the first transfer section and draws in the reference solution delivered to the flow channel, and which delivers the sample solution supplied to the inlet section, following the reference solution, to the detecting section of the flow channel.

7. The flow cell according to claim 2,
wherein the inlet section accumulates an amount of the reference solution, which partially remains in the inlet section, in an equilibrium state where the reference solution has been delivered to the flow channel and the liquid delivery has been stopped.

8. The flow cell according to claim 2,
wherein the reserve section includes a liquid sealed member having a closed container shape and connected to the inlet section, and
the reference solution accumulated in the inlet section is delivered to the detecting section by unsealing the liquid sealed member.

9. The flow cell according to claim 2,
wherein the reserve section includes a sheet-shaped inlet section sealing member having a sheet shape and sealing an opening of the inlet section, and
the reference solution accumulated in the inlet section is delivered to the detecting section by unsealing the inlet section sealing member.

10. The flow cell according to claim 2,
wherein the first transfer section includes a first through hole, one end of which communicates with the flow channel and an other end of which opens to outside air,
there is provided a first sealing member which seals an opening of the first through hole, and
the reference solution accumulated in the inlet section is delivered to the detecting section by unsealing the first sealing member.

11. The flow cell according to claim 6,
wherein the second transfer section includes a second through hole, one end of which communicates with the first transfer section and an other end of which opens to outside air,
there is provided a second sealing member which seals an opening of the second through hole, and
the sample solution supplied to the inlet section is delivered to the detecting section by unsealing the second sealing member.

* * * * *